United States Patent
Cheng et al.

(10) Patent No.: US 12,172,976 B2
(45) Date of Patent: Dec. 24, 2024

(54) DELOCALIZED LIPOPHILIC CATION COMPOUNDS AND METHODS OF USE THEREOF

(71) Applicant: The Board of Trustees of the Leland Stanford Junior University, Stanford, CA (US)

(72) Inventors: Zhen Cheng, Mountain View, CA (US); Hao Chen, Shanghai (CN)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 334 days.

(21) Appl. No.: 17/420,254

(22) PCT Filed: Jan. 10, 2020

(86) PCT No.: PCT/US2020/013136
§ 371 (c)(1),
(2) Date: Jul. 1, 2021

(87) PCT Pub. No.: WO2020/150103
PCT Pub. Date: Jul. 23, 2020

(65) Prior Publication Data
US 2022/0064140 A1 Mar. 3, 2022

Related U.S. Application Data

(60) Provisional application No. 62/792,703, filed on Jan. 15, 2019.

(51) Int. Cl.
*C07D 401/06* (2006.01)
*C09B 23/10* (2006.01)

(52) U.S. Cl.
CPC .......... *C07D 401/06* (2013.01); *C09B 23/105* (2013.01)

(58) Field of Classification Search
CPC .................................................. C07D 401/06
See application file for complete search history.

(56) References Cited

U.S. PATENT DOCUMENTS

| | | |
|---|---|---|
| 2005/0054006 A1 | 3/2005 | Chang et al. |
| 2007/0006396 A9 | 1/2007 | Rondeau |
| 2015/0336993 A1 | 11/2015 | Cheng |

FOREIGN PATENT DOCUMENTS

| | | |
|---|---|---|
| CN | 106279105 A | 1/2017 |
| CN | 106317018 A | 1/2017 |
| JP | 2000-63246 A | 2/2000 |
| WO | WO2009037325 A2 | 3/2009 |

OTHER PUBLICATIONS

Finkelstein, et al. U.S. Pat. No. 2,695,290, Nov. 23, 1954, retrieved from STN: Accession No. 1955:84530.*
Wu, et al. Chem. Commun. 2014, 50, 8919-8922.*
Malleron, et al. Journal of Medicinal Chemistry (1993), 36(15), 2242 (abstract), retrieved from STN: Accession No. 1993:517168, CAPLUS.*
Nishio, et al. JP 04251242 (abstract), Sep. 7, 1992, retrieved from STN: Accession No. 1993:505750, CAPLUS.*
Pubchem, 4-[2-(1H-Indol-3-yl)ethenyl]-1-methylpyridinium, Mar. 26, 2005, pp. 1-11 [online], [retrieved on Mar. 2, 2020], Retrieved from the Internet <URL:https://pubchem.ncbi.nlm.nih.gov/compound/423846>; p. 2.
Fun et al., Bis{4-[(E)-2-(1H-indol-3-yl)ethen-yl]-1-methylpyridinium} 4-fluoro-benzene-sulfonate nitrate 0.25-hydrate, Acta Crystallogr Sect E, Published online Nov. 9, 2013, vol. 69, Pt12, E69, pp. o1753-o1754.
Notice of Reasons for Refusal for Japan Application No. 2021-541174 mailed Oct. 4, 2022, with its English translation, 23 pages.
Wang et al., Uncoupling Effect of F16 Is Responsible for Its Mitochondrial Toxicity and Anticancer Activity, Toxicological Sciences, vol. 161, Issue 2, Feb. 2018, pp. 431-442.
Wang et al., Investigating the interactions of a novel anticancer delocalized lipophilic cation and its precursor compound with human serum albumin, RSC Adv., 2014, 4, 18205-18216.
Liu et al., A novel delocalized lipophilic cation-chlorambucil conjugate inhibits P-glycoprotein in HepG2/ADM cells, Bioorg Med Chem, Oct. 1, 20175; 25(20):5461-5467.
Xu et al., Pyridinium and indole orientation determines the mitochondrial uncoupling and anti-cancer efficiency of F16, Eur J Med Chem, Jun. 2, 20185; 154:305-313.
Liu et al., A photostable fluorescent probe for rapid monitoring and tracking of a trans-membrane process and mitochondrial fission and fusion dynamics, New J. Chem., 2016, 40, 3726-3731.
Fortuna et al., Synthesis and applications of new trans 1-indolyl-2-(1-methylpyridinium and quinolinium-2-yl) ethylenes, Apr. 2009, ARKIVOC 2009(8):122-129.
Garcia-Perez et al., Dequalinium induces cytotoxicity in human leukemia NB4 cells by downregulation of Raf/MEK/ERK and PI3K/Akt signaling pathways and potentiation of specific inhibitors of these pathways, Leuk Res, Jul. 2014; 38 (7):795-803.
RN 1107176-37-3 Registry, Database Registry, Aug. 24, 2022 [Online] Retrieved from STN.

(Continued)

*Primary Examiner* — Shawquia Jackson
(74) *Attorney, Agent, or Firm* — Bret E. Field; Bozicevic, Field & Francis LLP

(57) ABSTRACT

Provided are delocalized lipophilic cation (DLC) compounds and methods of using such compounds. Also provided are pharmaceutical compositions that include a DLC compound. Provided methods include methods of killing cells and methods of fluorescently labeling mitochondria by contacting the cells with a DLC compound of the present disclosure. Also provided are methods of imaging cell mitochondria, methods of determining whether a patient has a mitochondria related disease, and methods of treating a patient for a mitochondria related disease. Kits that include compounds of the present disclosure are also provided.

10 Claims, 12 Drawing Sheets

(56) References Cited

OTHER PUBLICATIONS

RN 1046786-49-5 Registry, Database Registry, Aug. 24, 2022 [Online] Retrieved from STN.
RN 1044512-26-6 Registry, Database Registry, Aug. 24, 2022 [Online] Retrieved from STN.
RN 339575-96-1 Registry, Database Registry, Aug. 24, 2022 [Online] Retrieved from STN.
RN 1107061-21-1 Registry, Database Registry, Aug. 24, 2022 [Online] Retrieved from STN.
RN 1106727-51-8 Registry, Database Registry, Aug. 24, 2022 [Online] Retrieved from STN.
RN 1105650-03-0 Registry, Database Registry, Aug. 24, 2022 [Online] Retrieved from STN.
RN 1033064-80-0 Registry, Database Registry, Aug. 24, 2022 [Online] Retrieved from STN.
RN 1025714-78-6 Registry, Database Registry, Aug. 24, 2022 [Online] Retrieved from STN.
Extended European Search Report for European Application No. 20740845.1 mailed Sep. 16, 2022, 8 pages.
Brown et al., Fluorescent neuroactive probes based on stilbazolium dyes, Org Biomol Chem, Apr. 7, 2011; 9 (7):2142-8.
Fantin et al., A novel mitochondriotoxic small molecule that selectively inhibits tumor cell growth, Cancer Cell vol. 2, Issue 1, Jul. 2002, pp. 29-42.
Fantin et al., F16, a mitochondriotoxic compound, triggers apoptosis or necrosis depending on the genetic background of the target carcinoma cell, Cancer Res, Jan. 1, 2004; 64(1):329-36.

\* cited by examiner

| Compound | Quantum Yield(%) |
|---|---|
| 1. 1-MeFF16 | 13.6 |
| 2. PhF16 | 12.2 |
| 3. 5BMF | 19.7 |
| 4. 5-BrF16 | 49.1 |
| 5. 2-PhF16 | 5.8 |
| 6. 5-CNF16 | 9.7 |
| 7. FF16 | 18.5 |
| 8. 2-ClF16 | 8.6 |
| 9. 2-Me-5-MeF16 | 18.1 |
| 10. 5-I-7-FF16 | 4.5 |
| 11. $NO_2F16$ | 1.24 |

FIG. 2C

| Compound | Cytotoxicity IC$_{50}$ (μM) | | | | Normal/Tumor Cell ratio | |
|---|---|---|---|---|---|---|
| | T24 | H838 | 3T3 | 3T3/T24 | 3T3/H838 |
| 1. 1-MeFF16 | 21.7 | 19.1 | 104.5 | 4.83 | 5.48 |
| 2. PhF16 | 1.02 | 1.50 | 0.29 | 0.28 | 0.20 |
| 3. 5BMF | 0.816 | 0.361 | 11.0 | 13.45 | 30.42 |
| 4. 5-BrF16 | 1.84 | 1.2 | 11.6 | 6.31 | 9.70 |
| 5. 2-PhF16 | 4.02 | 3.74 | 0.326 | 0.08 | 0.09 |
| 6. 5-CNF16 | 316 | 20 | 21250 | 671.83 | 1030.32 |
| 7. FF16 | 6.26 | 3.63 | 75.1 | 11.99 | 20.67 |
| 8. 2-ClF16 | 54.7 | 25.7 | 13.8 | 0.25 | 0.54 |
| 9. 2-Me-5-MeF16 | 68.8 | 17.3 | 161.3 | 2.34 | 9.34 |
| 10. 5-i-7-FF16 | 3.83 | 1.29 | 14.2 | 3.71 | 11.03 |
| 11. NO$_2$F16 | 73.8 | 4.70 | 86.0 | 1.16 | 18.30 |

FIG. 4

FIG. 5A
| Cell line | Cytotoxicity IC$_{50}$ (µM) 5BMF |
|---|---|
| 1. H838 | 0.36 |
| 2. HCC4006 | 0.106 |
| 3. HCC827 | 1.99 |
| 4. H1693 | 1.18 |
| 5. H2030 | 0.102 |
| 6. H2228 | 0.0489 |
| 7. A549 | 0.727 |
| 8. H1437 | 1.43 |
| 9. H1944 | 0.261 |
FIG. 5B
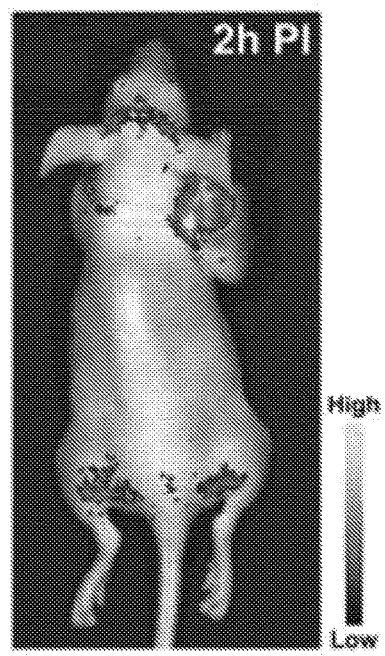
FIG. 5C
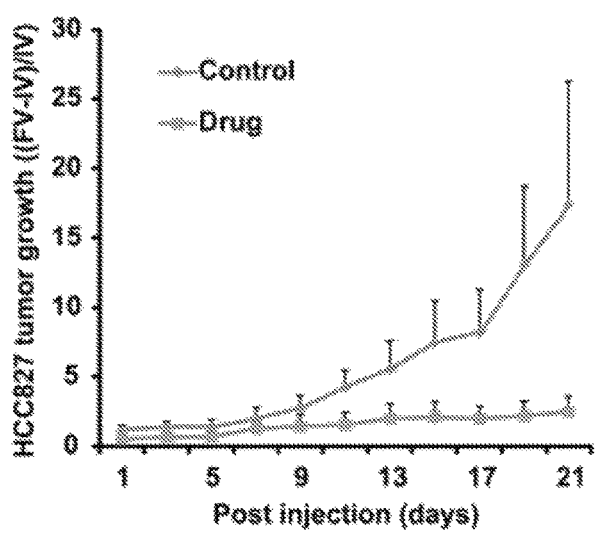
FIG. 5D
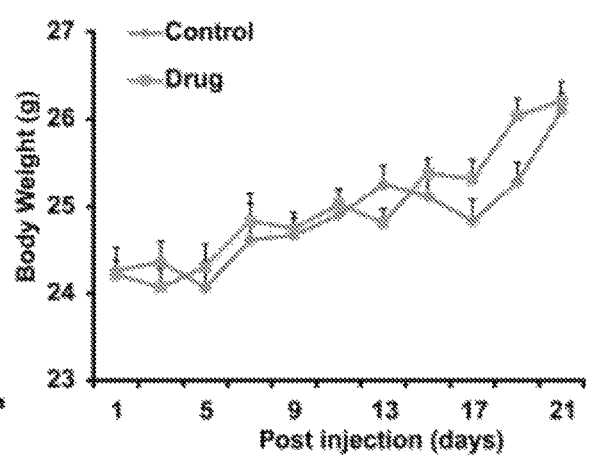

Panel A

Panel B

Panel A

Panel B

Panel C

Panel D

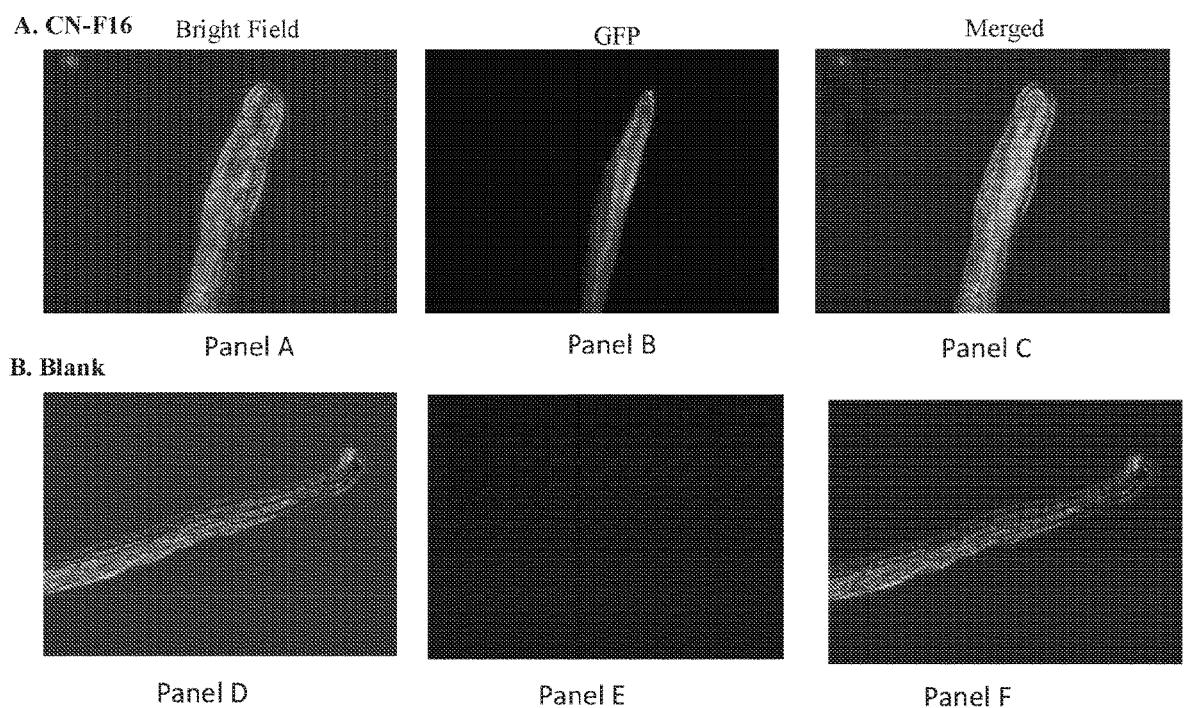
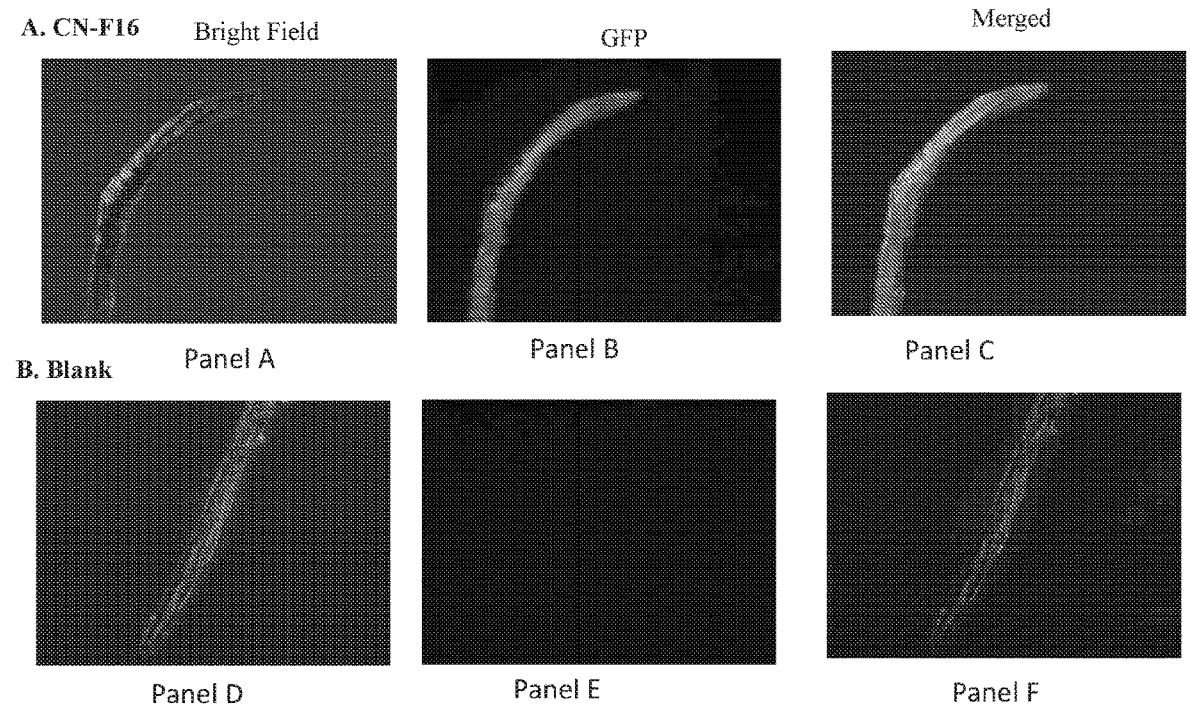

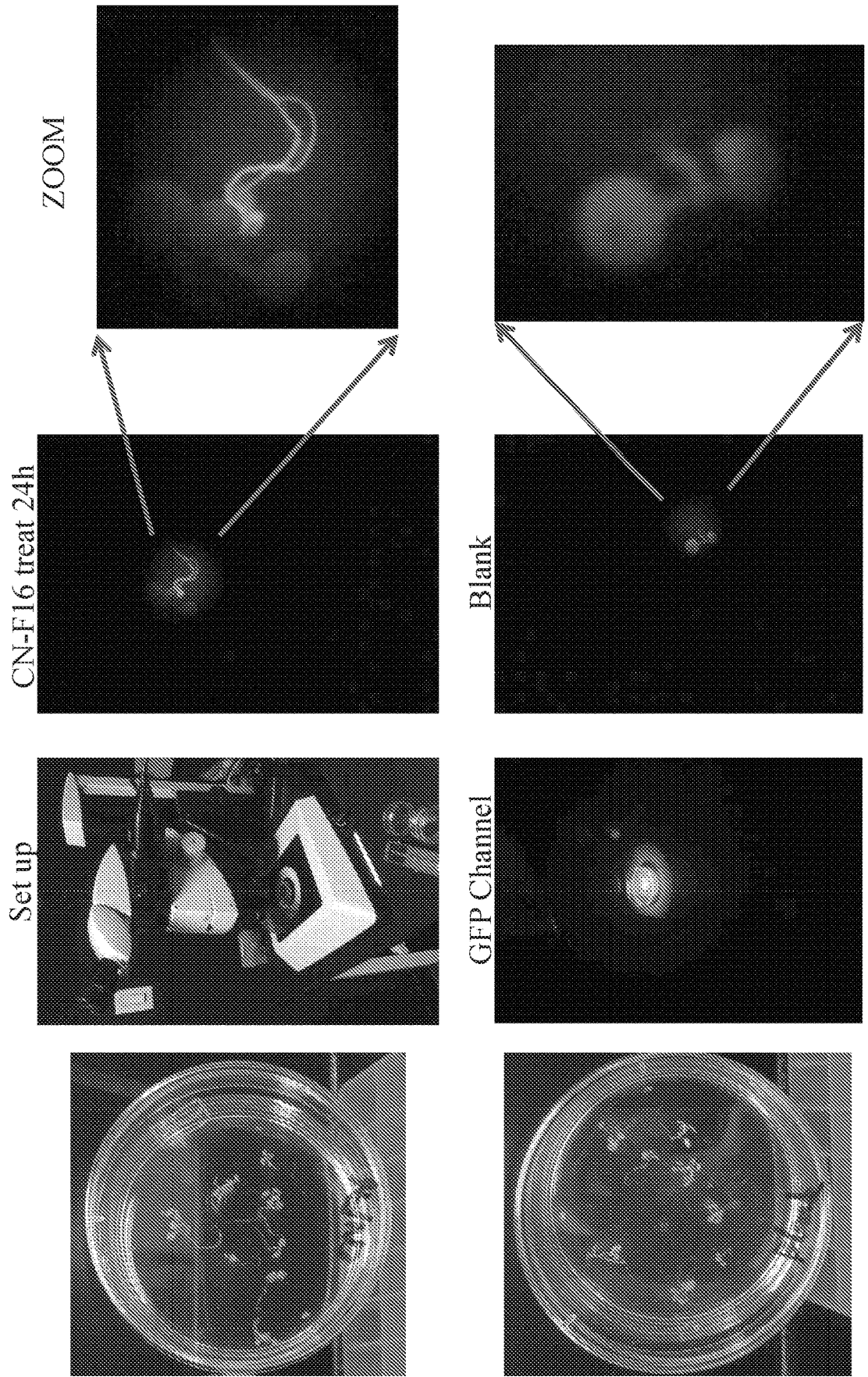

DELOCALIZED LIPOPHILIC CATION COMPOUNDS AND METHODS OF USE THEREOF

CROSS-REFERENCE TO RELATED APPLICATION

This application is a U.S. National Stage Application of PCT Application No. PCT/US2020/013136 filed Jan. 10, 2020, which application, pursuant to 35 U.S.C. § 119(e), claims priority to the filing date of U.S. Provisional Patent Application No. 62/792,703, filed Jan. 15, 2019, which applications are incorporated herein by reference in its entirety.

GOVERNMENT RIGHTS

This invention was made with Government support under grant no. DE-SC0008397 awarded by the U.S. Department of Energy. The Government has certain rights in this invention.

INTRODUCTION

Cancer causes enormous burdens on society. In fact, the world population experienced an estimated 18.1 million new cases of cancer in 2018. Traditionally, cancer treatment involved chemical or biological compounds (chemotherapy), radiation (radiotherapy), or surgery. However, although such treatments are effective in some cases, they are ineffective in others. In addition, surgical resection of cancerous tissues sometimes use insufficient margins and the cancer reoccurs.

Delocalized lipophilic cations (DLCs) have been utilized as fluorescent dyes and have been investigated as possible chemotherapeutic drugs for the treatment of cancer. Certain DLCs have been shown to be cytotoxic to cancer cells, and to accumulate within the mitochondria of cancerous cells. However, many DLCs have low cytotoxicity to cancer cells and structure-activity relationships that remains poorly understood.

SUMMARY

Provided are delocalized lipophilic cation (DLC) compounds and methods of using such compounds. Also provided are pharmaceutical compositions that include a DLC compound. Provided methods include methods of killing cells and methods of fluorescently labeling mitochondria by contacting the cells with a DLC compound of the present disclosure. Also provided are methods of imaging cell mitochondria, methods of determining whether a patient has a mitochondria related disease, and methods of treating a patient for a mitochondria related disease. Kits that include compounds of the present disclosure are also provided.

BRIEF DESCRIPTION OF THE FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2C shows the fluorescent quantum yield of compounds (1) through (11).

FIG. 4 shows the cytotoxicity of compounds (1) through (11) for T24, H838, and 3T3 cells.

FIG. 5A shows the cytotoxicity $IC_{50}$ of compound (3) in nine lung cancer cell lines.

FIG. 5B shows a representative in vivo fluorescent image of a human lung cancer HCC827 bearing mouse after 2 h post injection (P1) of compound (3).

FIG. 5C shows the effects of compound (3) on the tumor growth of HCC827 in nude mice (n=10 per group).

FIG. 5D shows the effects of compound (3) (15 mg/kg) on the nude body weight of tumor bearing nude mice versus a control group (PBS).

FIG. 8 shows the fluorescent labeling of *Arabidopsis thaliana* root after 1 hour by compound (6).

FIG. 9 shows the fluorescent labeling of *Arabidopsis thaliana* root after 20 hours by compound (6).

FIG. 10 shows the experimental setup used to capture *Arabidopsis thaliana* whole plant images.

DEFINITIONS

Figure 1:
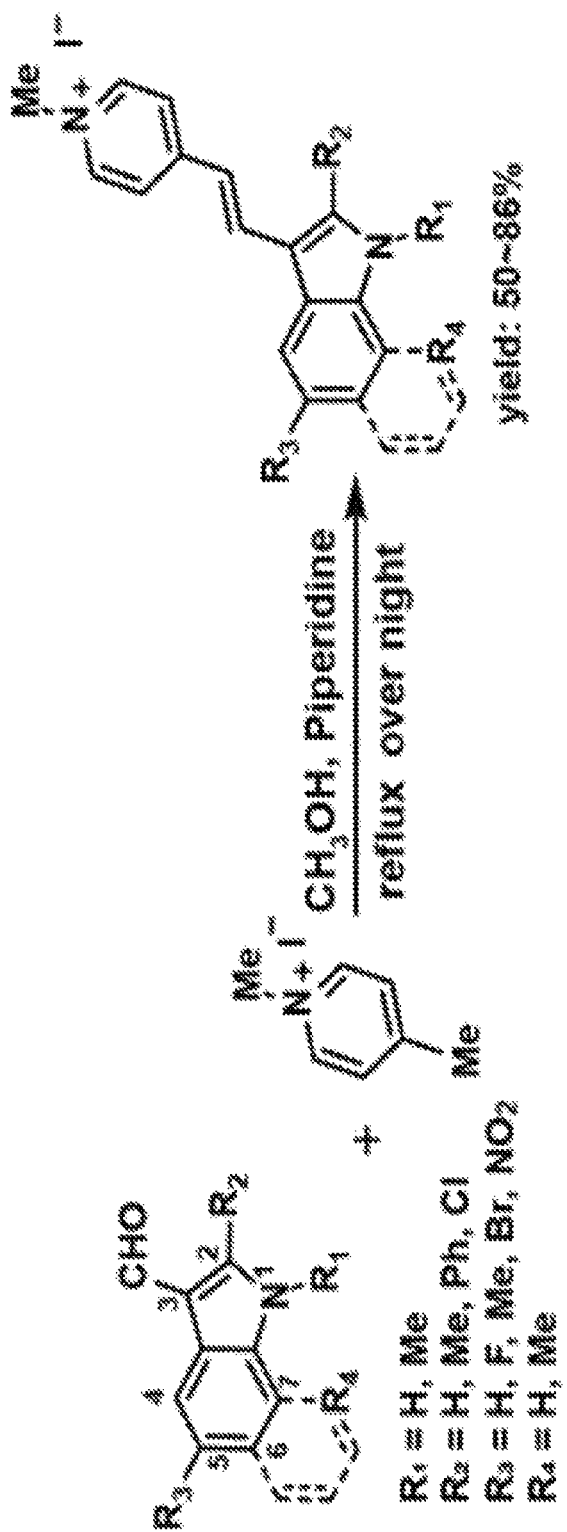
FIG. 1 shows synthetic schemes used to synthesize compounds (1) through (11).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with cancer, e.g. those having tumors) as well as those in which prevention is desired (e.g., those with increased susceptibility to cancer; those with cancer; those suspected of having cancer; etc.).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

A "therapeutically effective amount", a "therapeutically effective dose" or "therapeutic dose" is an amount sufficient to effect desired clinical results (i.e., achieve therapeutic efficacy, achieve a desired therapeutic response, etc.). A therapeutically effective dose can be administered in one or more administrations. For purposes of this disclosure, a therapeutically effective dose of a composition is an amount that is sufficient, when administered to the individual, to palliate, ameliorate, stabilize, reverse, prevent, slow or delay the progression of a disease state (e.g., cancer, etc.) present in the subject.

Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or *Vogel, A Textbook of Practical Organic Chemistry, Including Qualitative Organic Analysis*, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Substituted alkylene" refers to an alkylene group having from 1 to 3 hydrogens replaced with substituents as described for carbons in the definition of "substituted" below.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^2$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" or "azide" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —C(O)O— alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

As used herein, "carbocycle" or "carbocyclic ring" is intended to mean any stable monocyclic, bicyclic, or tricyclic ring having the specified number of carbons, any of which may be saturated, unsaturated, or aromatic. For example a C3-14 carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when a covalent bond or one or more carbon atoms link two non-adjacent carbon atoms in a ring. In one embodiment, bridge rings are one or two carbon atoms. It is noted that a bridge always converts a monocyclic ring into a bicyclic ring. When a ring is bridged, the substituents recited for the ring may also be present on the bridge. Fused (e.g., naphthyl and tetrahydronaphthyl) and spiro rings are also included.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$— heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO— alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with $=O$, $=NR^{70}$, $=N-OR^{70}$, $=N_2$ or $=S$) on saturated carbon atoms in the specified group or radical are, unless otherwise specified, —$R^{60}$, halo, $=O$, —$OR^{70}$, —$SR^{70}$, —$NR^{80}R^{80}$, trihalomethyl, —CN, —OCN, —SCN, —NO, —$NO_2$, $=N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —ON, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)R^{70}$, —$C(O)NR^{80}R^{80}$, —$C(NR^{70})NR^{80}R^{80}$, —$OC(O)R^{70}$, —$OC(S)R^{70}$, —$CO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$—$NR^{70}CO_2R^{70}$, —$NR^{70}C(S)OR^{70}$, —$NR^{70}C(O)NR^{70}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH$_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH$_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), epidithio (—S—S—), carbonyldioxy (—O—CO—O—), alkyldioxy (—O—(CH2)n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$)alkyl), which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

As used herein, the terms "terminal group" or "end group" are used interchangeably to refer to the groups located at the terminals of the endosomal disruptor e.g. as described herein. Terminal groups of interest include, but are not limited to a terminal capping group, such as H, an aryl, a substituted aryl, a heteroaryl, a substituted heteroaryl, an alkyl or a substituted alkyl. In certain cases, the terminal group may be defined as a chemoselective group (e.g. as described herein).

As used herein, the term "hydrophilic group" by itself refers to a monovalent or multivalent group which includes a hydrophilic moiety and an optional linker. In some cases, a hydrophilic group is attached to the hydrophilic masking moiety and the hydrophilic tail moiety of the subject endosomal disruptors. The hydrophilic moiety is a moiety that is well solvated in aqueous environments, e.g., under reverse phase (RP) chromatography conditions, and that imparts increased water solubility on the group to which it is attached or incorporated (e.g., the linker). In some cases, the hydrophilic moiety is referred to as a hydrophilic functional group. In some cases, the hydrophilic moiety is a heterocycle. In certain cases, the hydrophilic moiety is a heteroaryl. In some cases, the hydrophilic moiety is charged (e.g., ionic). In some cases, the hydrophilic moiety is polar and neutral (e.g., non-ionic). It is understood that certain functional groups may be present in either an ionic or a non-ionic form, dependent on the surrounding conditions, e.g., solvent, pH and the like, and that all such forms of the hydrophilic moieties described herein are meant to be included in the present disclosure. For example, the hydrophilic moiety can be a basic group which is neutral until protonated, e.g., under aqueous conditions of a suitable pH, or the hydrophilic moiety can be an acidic group which is neutral until deprotonated, e.g., under aqueous conditions of a suitable pH.

A hydrophilic moiety can increase the solubility of the group to which it is attached in a predominantly aqueous solution, as compared to a control group which lacks the hydrophilic moiety. A hydrophilic moiety is different from a hydrophobic moiety which is not well solvated in aqueous environments. In certain instances, a hydrophilic group includes at least one neutral polar functional group per 5 carbons, or at least one charged functional group per 7 carbons. In some instances, a hydrophilic group (e.g., the hydrophilic group in isolated form as a discrete molecule) has solubility in water of at least 1% by weight.

Hydrophilic groups and hydrophilic moieties of interest include, but are not limited to, Nitrogen-containing heterocycle, amide, carbamate, carboxylic acid carboxy ester, methyl ether, cyano, amine, sulfonamide, sulfonate, urea, thiourea, sulfonic acid, carboxylate, phosphonate, phosphate, sulfate, sulfinate, sulfonium, polyethylene glycols (PEG) and modified PEGs, hydroxyl, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M, —PO$_3$M', —NR$^{3+}$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$_{yy'}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$_{zz}$, and R$_{zz}$ and R$_{yy'}$ are independently selected from H and C$_{1-3}$ alkyl. In some cases, a hydrophilic moiety is (CH$_2$)$_x$(OCH$_2$CH$_2$)$_y$OCH$_3$ where each x is independently an integer from 0-20, each y is independently an integer from 0 to 50.

Nitrogen-containing heterocycles of interest that find use as hydrophilic moieties include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, and substituted versions thereof.

As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a functional group (e.g., as described herein). Any convenient linking groups may be utilized at the terminal of a PEG to connect the group to a moiety of interest including but not limited to, alkyl, aryl, hydroxyl, amino, acyl, acyloxy, carboxyl ester and amido terminal and/or substituent groups.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

In certain embodiments, a substituent may contribute to optical isomerism and/or stereo isomerism of a compound. Salts, solvates, hydrates, and prodrug forms of a compound are also of interest. All such forms are embraced by the present disclosure. Thus, the compounds described herein include salts, solvates, hydrates, prodrug and isomer forms thereof, including the pharmaceutically acceptable salts, solvates, hydrates, prodrugs and isomers thereof. In certain embodiments, a compound may be metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

Definitions of other terms and concepts appear throughout the detailed description below.

DETAILED DESCRIPTION

Provided are delocalized lipophilic cation (DLC) compounds and methods of using such compounds. Also provided are pharmaceutical compositions that include a DLC compound. Provided methods include methods of killing cells and methods of fluorescently labeling mitochondria by contacting the cells with a DLC compound of the present disclosure. Also provided are methods of imaging cell mitochondria, methods of determining whether a patient has a mitochondria related disease, and methods of treating a patient for a mitochondria related disease. Kits that include compounds of the present disclosure are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, the present disclosure provides compounds that include delocalized lipophilic cation compounds. Such delocalized lipophilic cation compounds find use in variety of different areas, including but not limited to e.g., killing cells by contacting a cell with the compound, fluorescently labeling cells, or subparts thereof, by contacting cells with the compound, and treating a subject for a condition by administering the compound or a pharmaceutical composition that includes the compound.

In some instances, compounds of the present disclosure selectively accumulate in the mitochondria of cancer cells. By "selectively accumulates in the mitochondria of cancer cells" generally means that the compound accumulates to a higher extent in the mitochondria of cancer cells relative to the mitochondria of normal (i.e., non-cancerous) cells. Without being bound by theory, a DLC may partially or fully dissipate the proton gradient across the inner mitochondrial membrane and may in some cases, cause necrosis of a cancer cell, cause apoptosis of a cancer cell, reduce the growth of a cancer cell, reduce the rate of mitosis of a cancer cell, or a combination thereof.

Also provided are pharmaceutical compositions that include the subject compounds, where a compound of the present disclosure can be formulated with a pharmaceutically acceptable excipient. Formulations may be provided in a unit dose, where the dose provides an amount of the compound effective to achieve a desired result. Desired results may vary and may include but are not limited to e.g., partially or fully dissipating the proton gradient across an inner mitochondrial membrane, causing necrosis of a cancer cell, causing apoptosis of a cancer cell, reducing the growth of a cancer cell, reducing the rate of mitosis of a cancer cell, or a combination thereof.

As summarized above, these compounds and methods find use in a variety of applications. Non-limiting examples of such applications include those in which partially or fully dissipating the proton gradient across an inner mitochondrial membrane, treating cancer, or both may be desired. These compounds may also find uses in other applications such as but not limited to e.g., photodynamic therapy, photothermal therapy, optical imaging, fluorescent image-guided surgery, and the like.

Compositions

The present disclosure provides delocalized lipophilic cation compounds. A delocalized lipophilic cation compound of the present disclosure comprises an aryl group, a linking group, and a third group comprising a positive charge, wherein the delocalized lipophilic cation compound is a π-conjugated system. The aryl group is linked to the third group by the linking group. As used herein, the term "π-conjugated system" means that the delocalized lipophilic cation compound comprises π-conjugation that includes the aryl group, the linker, and the third group comprising a positive charge. In some cases, the aryl group can be a substituted aryl group, a heteroaryl group, or a substituted heteroaryl group.

In some cases, the delocalized lipophilic cation compound is of the formula (I):

A-L-Z+            (1)

wherein:
A is selected from aryl, substituted aryl, heteroaryl and substituted heteroaryl;
L is a linker;
$Z^+$ is a group comprising a positive charge,
wherein the compound is a T-conjugated system.

Group A

In some embodiments of formula (I), group A has the structure (A1):

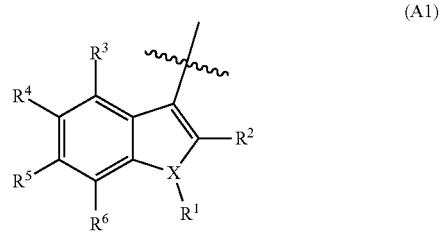

wherein:
X is selected from $CR^8$ and N;
$R^1$ is selected from H, alkyl, substituted alkyl, alkenyl, substituted alkenyl, aryl, substituted aryl, heteroaryl and substituted heteroaryl;
$R^2$, $R^3$ and $R^4$ are each independently selected from H, alkyl, substituted alkyl, alkenyl, substituted alkenyl, aryl, substituted aryl, heteroaryl, substituted heteroaryl, halogen, nitro and nitrile;

$R^5$ and $R^6$ are each independently selected from H, alkyl, substituted alkyl, alkenyl, substituted alkenyl, aryl, substituted aryl, heteroaryl, substituted heteroaryl, halogen, nitro and nitrile; or $R^5$ and $R^6$ together with the carbon atoms to which they are attached form a fused ring selected from aryl, substituted aryl, heteroaryl and substituted heteroaryl.

In some embodiments of formula (I), group A is an indole or a substituted indole. In some cases, group A has the structure (A2):

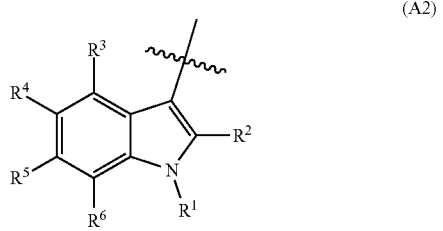

(A2)

wherein:
$R^1$ is selected from H, alkyl, substituted alkyl, alkenyl, substituted alkenyl, aryl, substituted aryl, heteroaryl and substituted heteroaryl;
$R^2$, $R^3$ and $R^4$ are each independently selected from H, alkyl, substituted alkyl, alkenyl, substituted alkenyl, aryl, substituted aryl, heteroaryl, substituted heteroaryl, halogen, nitro and nitrile;
$R^5$ and $R^6$ are each independently selected from H, alkyl, substituted alkyl, alkenyl, substituted alkenyl, aryl, substituted aryl, heteroaryl, substituted heteroaryl, halogen, nitro and nitrile; or $R^5$ and $R^6$ together with the carbon atoms to which they are attached form a fused ring selected from aryl, substituted aryl, heteroaryl and substituted heteroaryl.

In some cases, group A has the structure (A3):

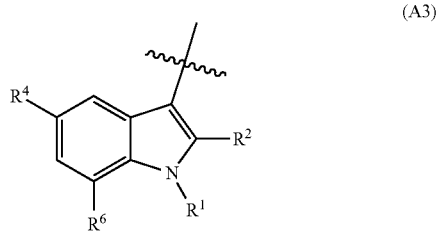

(A3)

wherein:
$R^1$ is selected from H, alkyl, substituted alkyl, alkenyl, substituted alkenyl, aryl, substituted aryl, heteroaryl and substituted heteroaryl;
$R^2$, $R^4$ and $R^6$ are each independently selected from H, alkyl, substituted alkyl, alkenyl, substituted alkenyl, aryl, substituted aryl, heteroaryl, substituted heteroaryl, halogen, nitro and nitrile.

In some cases wherein group A has the structure A3, $R^1$ is H. In some cases, $R^1$ is alkyl, e.g. methyl. In some cases, $R^2$ is H. In some cases, $R^2$ is alkyl, e.g. methyl. In some cases, R is H. In some cases, $R^4$ is alkyl, e.g. methyl. In some cases, $R^4$ is a halogen, e.g. bromide. In some cases, $R^4$ is nitro. In some cases, $R^4$ is nitrile. In some cases, $R^6$ is H. In some cases, R is alkyl, e.g. methyl.

In some cases wherein group A has the structure A3, $R^3$ is an electron withdrawing group. In some cases, $R^4$ is an electron-donating group.

In some embodiments of formula (I), group A has the structure (A4):

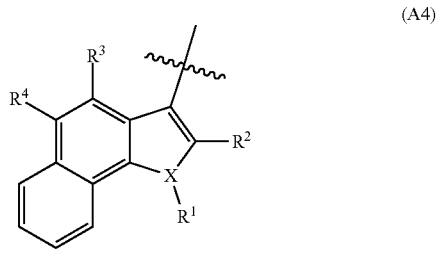

(A4)

wherein:
X is selected from $CR^8$ and N;
$R^1$ and $R^8$ are each independently selected from H, alkyl, substituted alkyl, alkenyl, substituted alkenyl, aryl, substituted aryl, heteroaryl and substituted heteroaryl;
$R^2$, $R^3$ and $R^4$ are each independently selected from H, alkyl, substituted alkyl, alkenyl, substituted alkenyl, aryl, substituted aryl, heteroaryl, substituted heteroaryl, halogen, nitro and nitrile.

In some cases wherein group A has the structure A4, X is CH. In some cases, $R^1$, $R^2$, $R^3$, and $R^4$ are each H.

Linker L

In some cases, group L is selected from alkenylene, alkynylene, arylene, alkarylene and aralkylene. In some cases, group L has the structure (L1):

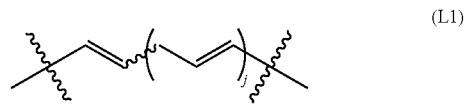

(L1)

wherein:
j is an integer from 0 to 10, and
the wavy line (i.e. 〰〰) denotes that the carbon-carbon double bond or bonds may be any combination of cis or trans.

In some cases wherein group L has the structure L1, j is 0, 1, 2, 3, 4, or 5. In some cases, j is zero. In some cases, j is zero and the carbon-carbon double bond is trans (i.e. group L has the structure (L2)):

(L2)

Group Z+

In some embodiments, Z+ is selected from a heteroaryl or substituted heteroaryl having a positive charge. In some cases, Z+ is a pyridinium or a substituted pyridinium. In some cases, Z+ has the structure (Z1):

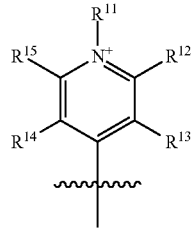

(Z1)

wherein:

$R^{11}$, $R^{12}$, $R^{13}$, $R^{15}$, and $R^{16}$ are each independently selected from H, alkyl, substituted alkyl, alkenyl, substituted alkenyl, aryl, substituted aryl, heteroaryl and substituted heteroaryl.

In some cases wherein Z+ has the structure Z1, $R^{11}$ is alkyl, e.g. methyl. In some cases, $R^{11}$, $R^{12}$, $R^{13}$, $R^{15}$, and $R^{16}$ are each H. In some cases, $R^{11}$ is methyl and $R^{12}$, $R^{13}$, $R^{14}$, and $R^{15}$ are each H (i.e. Z+ has the structure (Z4)):

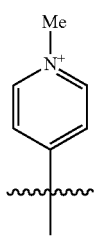

(Z2)

In some cases, Z+ is a pyridinium or a substituted pyridinium. In some cases, Z+ has the structure (Z3):

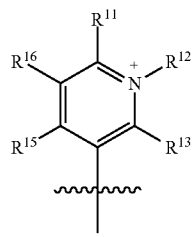

(Z3)

wherein:

$R^{11}$, $R^{12}$, $R^{13}$, $R^{15}$, and $R^{16}$ are each independently selected from H, alkyl, substituted alkyl, alkenyl, substituted alkenyl, aryl, substituted aryl, heteroaryl and substituted heteroaryl.

In some cases, Z+ is a pyridinium or a substituted pyridinium. In some cases, Z+ has the structure (Z4):

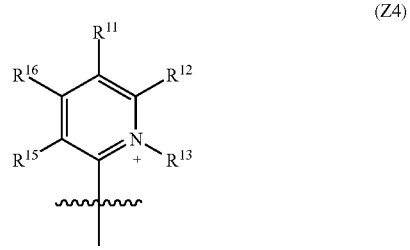

(Z4)

wherein:

$R^{11}$, $R^{12}$, $R^{13}$, $R^{15}$, and $R^{16}$ are each independently selected from H, alkyl, substituted alkyl, alkenyl, substituted alkenyl, aryl, substituted aryl, heteroaryl and substituted heteroaryl.

Delocalized Lipophilic Cation Compounds

In some embodiments of formula (I), the delocalized lipophilic cation compound is of the formula (II):

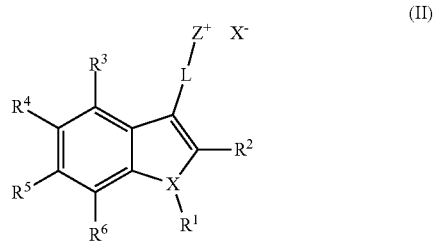

(II)

wherein:

X− is a counterion;

L is a linker;

Z+ is a group comprising a positive charge;

$R^1$ is selected from H, alkyl, substituted alkyl, alkenyl, substituted alkenyl, aryl, substituted aryl, heteroaryl and substituted heteroaryl;

$R^2$, $R^3$ and $R^4$ are each independently selected from H, alkyl, substituted alkyl, alkenyl, substituted alkenyl, aryl, substituted aryl, heteroaryl, substituted heteroaryl, halogen, nitro and nitrile; and $R^5$ and $R^6$ are each independently selected from H, alkyl, substituted alkyl, alkenyl, substituted alkenyl, aryl, substituted aryl, heteroaryl, substituted heteroaryl, halogen, nitro and nitrile; or $R^5$ and $R^6$ together with the carbon atoms to which they are attached form a fused ring selected from aryl, substituted aryl, heteroaryl and substituted heteroaryl.

In some embodiments of formula (II), L has a structure selected from L1 and L2. In some embodiments of formula (II), Z+ has a structure selected from Z1, Z2, Z3, and Z4. In some embodiments of formula (II), L has a structure selected from L1 and L2 and Z+ has a structure selected from Z1, Z2, Z3, and Z4.

In some embodiments of formulae (I) or (II), the delocalized lipophilic cation compound is of the formula (III):

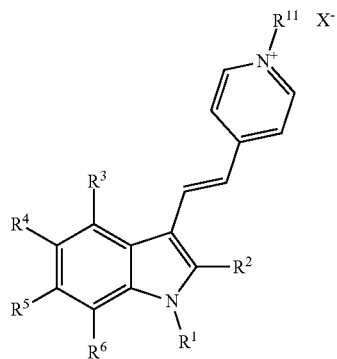

(III)

wherein:

X⁻ is a counterion;

R¹ is selected from H, alkyl, substituted alkyl, alkenyl, substituted alkenyl, aryl, substituted aryl, heteroaryl and substituted heteroaryl;

R², R³ and R⁴ are each independently selected from H, alkyl, substituted alkyl, alkenyl, substituted alkenyl, aryl, substituted aryl, heteroaryl, substituted heteroaryl, halogen, nitro and nitrile;

R⁵ and R⁶ are each independently selected from H, alkyl, substituted alkyl, alkenyl, substituted alkenyl, aryl, substituted aryl, heteroaryl, substituted heteroaryl, halogen, nitro and nitrile; or R⁵ and R⁶ together with the carbon atoms to which they are attached form a fused ring selected from aryl, substituted aryl, heteroaryl and substituted heteroaryl; and R¹¹ is selected from H, alkyl, substituted alkyl, alkenyl, substituted alkenyl, aryl, substituted aryl, heteroaryl and substituted heteroaryl.

In some embodiments of formula (III), at least one of R¹, R², R³, R⁴, R⁵ and R⁶ is a substituent other than hydrogen. In some embodiments of formula (II), X⁻ is iodide.

In some embodiments of formulae (I) to (III), the delocalized lipophilic cation compound is of the formula (IV):

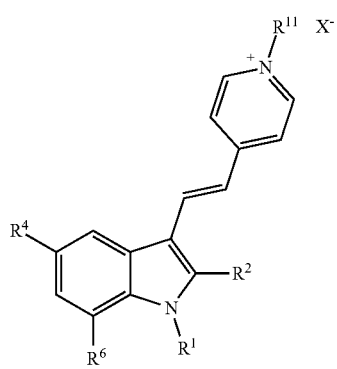

(IV)

wherein:

X⁻ is a counterion;

R¹ is selected from H, alkyl, substituted alkyl, alkenyl, substituted alkenyl, aryl, substituted aryl, heteroaryl and substituted heteroaryl;

R², is selected from H, alkyl, substituted alkyl, alkenyl, substituted alkenyl, aryl, substituted aryl, heteroaryl, substituted heteroaryl, halogen, nitro and nitrile;

R⁶ is selected from H, alkyl, substituted alkyl, alkenyl, substituted alkenyl, aryl, substituted aryl, heteroaryl, substituted heteroaryl, halogen, nitro and nitrile; or R and R together with the carbon atoms to which they are attached form a fused ring selected from aryl, substituted aryl, heteroaryl and substituted heteroaryl; and R¹¹ is selected from H, alkyl, substituted alkyl, alkenyl, substituted alkenyl, aryl, substituted aryl, heteroaryl and substituted heteroaryl.

In some embodiments of formula (IV), at least one of R¹, R², R⁴, and R⁶ is a substituent other than hydrogen. In some embodiments of formula (III), X⁻ is iodide.

In some embodiments of formulae (I) through (IV), the delocalized lipophilic cation compound is a derivative of F16, wherein F16 has the structure (F16):

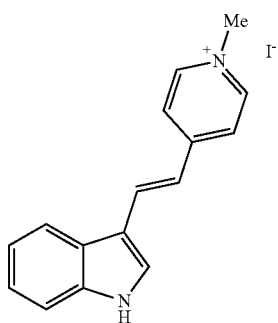

(F16)

In some embodiments of formulae (I) to (III), the delocalized lipophilic cation compound has a structure selected from:

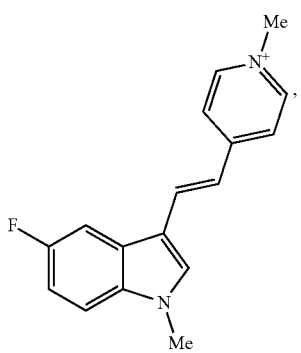

(1)

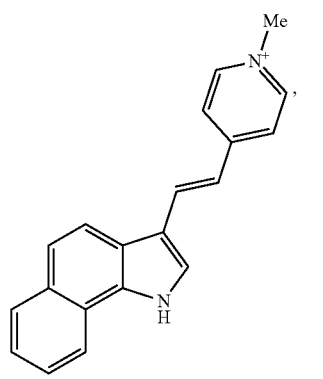 (2)
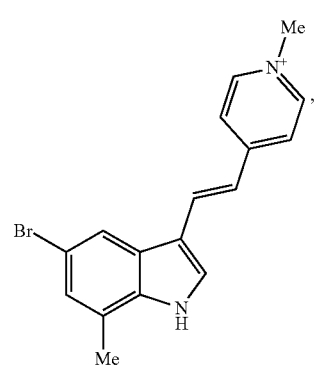 (3)
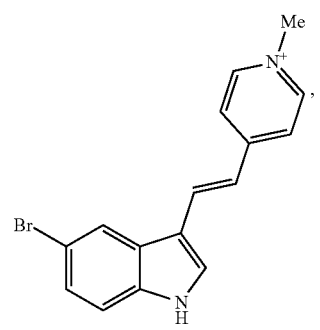 (5)
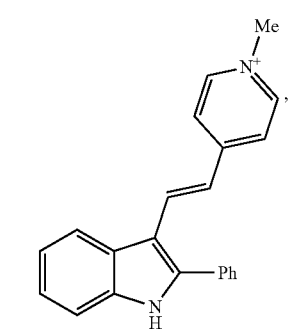 (6)
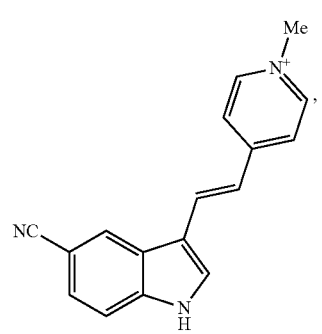 (4)
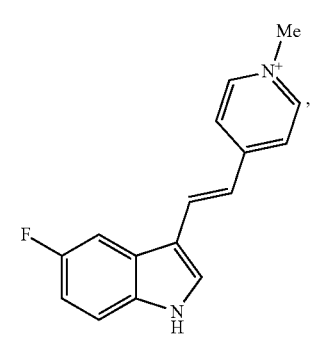 (7)
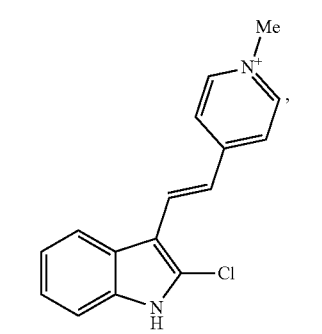 (8)
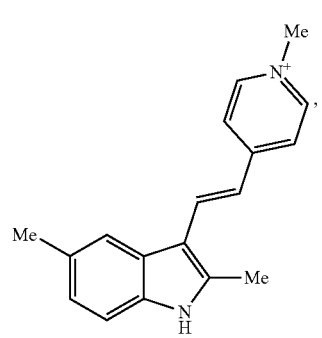 (9)
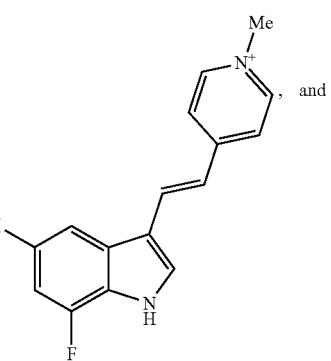 , and (10)

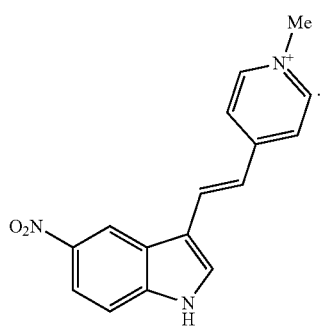

(11)

As used herein, the compound (3) is also interchangeably referred to as 5BMF.

In some embodiments of formulae (I) to (IV), the delocalized lipophilic cation compound has the structure:

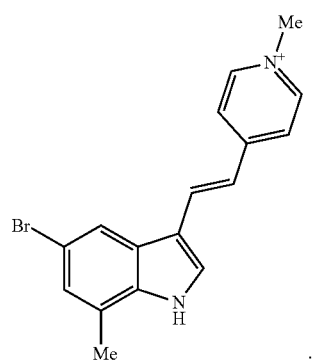

(3)

In some cases, the delocalized lipophilic cation compounds are cytotoxic. In some cases, the compounds are selectively cytotoxic to cancer cells, i.e. they have greater cytotoxicity to cancer cells as compared to the cytotoxicity of the compound to normal cells. In some cases, the compounds are selectively cytotoxic by a factor of 2 or more, such as 3 or more, 4 or more, 5 or more, 10 or more, 20 or more, 50 or more, or 100 or more.

In some cases, the compounds have a cytotoxicity half maximal inhibitory concentration (i.e. cytotoxicity $IC_{50}$) for cancer cells of 100 µM or less, such as 50 µM or less, 25 µM or less, 10 µM or less, 5 µM or less, 1 µM or less, 500 nM or less, 250 nM or less, or 100 nM or less. In some cases, the compounds have a cytotoxicity $IC_{50}$ for cancer cells that is greater than the cytotoxicity $IC_{50}$ for normal cells. In some cases, the ratio cytotoxicity $IC_{50}$ for cancer cells to cytotoxicity $IC_{50}$ for normal cells is 2 or greater, such as 3 or greater, 4 or greater, 5 or greater, 10 or greater, 20 or greater, 50 or greater, or 100 or greater.

In some cases, the compounds have a fluorescence absorbance peak between 350 nm and 500 nm, such as between 375 nm and 475 nm, between 400 nm and 450 nm, or between 400 nm and 425 nm. In some cases, the compounds have a fluorescence emission peak between 475 nm and 575 nm, such as between 490 nm and 550 nm, or between 500 nm and 525 nm.

In some cases, the compounds have a fluorescence quantum yield of 5% or more relative to a reference standard. Suitable reference standards will vary and may include various fluorescent molecules including but not limited to e.g., fluorescein, rhodamine, N,N,N',N'-Tetramethylacridine-3,6-diamine (acridine orange), allophycocyanin, chlorophyll, propidium iodide, 4',6-diamidino-2-phenylindole (DAPI), Hoechst 33342, R-phycoerythrin, etc. In some cases, the compounds have a fluorescence quantum yield of 5% or more relative to a Rhodamine 6G reference, such as 10% or more, 15% or more, 20% or more, 25% or more, 30% or more, or 40% or more. In some cases, the compounds have a fluorescence quantum yield of 10% or more relative to a Rhodamine 60 reference. In some cases, the compounds have a fluorescence quantum yield of 10% or more relative to a Rhodamine 6G reference in an ethanol solvent.

In some cases, the compounds accumulate in the mitochondria of cells. In some cases, the compounds selectively accumulate in the mitochondria of cancer cells. Selective accumulation of the compound may refer to the accumulation of the compounds in the mitochondria of cancer cells that is greater than the accumulation of the compounds in the mitochondria of normal cells. In some cases, the compounds selectively accumulate in the mitochondria of cancer cells by a factor of 2 or more, 3 or more, 4 or more, 5 or more, 10 or more, 20 or more, 50 or more, or 100 or more.

In some cases, the compounds may cause apoptosis of cancer cells. In some cases, the compounds may cause necrosis of cancer cells. In some case, apoptosis and/or necrosis caused by a compound of the present disclosure may be selective for cancer cells, i.e., the apoptosis and/or necrosis caused by a compound of the present disclosure is increased in cancer cells as compared to normal (i.e., non-cancerous) cells. In some cases, the compounds reduce the rate of growth of a tumor. In some cases, the compounds reduce the size of a tumor.

Pharmaceutical Compositions

A pharmaceutical composition comprising a subject compound (i.e., a delocalized lipophilic cation compound or a combination thereof) may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences,* 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. In some instances, a topical preparation of a medicament useful in the methods described herein may include, e.g., an ointment preparation that includes one or more excipients including, e.g., mineral oil, paraffin, propylene carbonate, white petrolatum, white wax and the like, in addition to one or more additional active agents.

Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

In some cases, the pharmaceutical composition may include a delocalized lipophilic cation compound and a pharmaceutically acceptable excipient.

Methods

As summarized above, compositions of the present invention may, in some instances, be used in the treatment of cancer. Compositions of the present invention may be used to treat various cancers including, but not limited to: Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sezary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenstrom Macroglobulinemia, Wilms Tumor, and the like.

As summarized above, compositions of the present invention may, in some instances, be used in the treatment of carcinomas. Compositions of the present invention may be used to treat various carcinomas including, but not limited to: acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchioloalveolar carcinoma, bronchogenic carcinoma, cholangiocellular carcinoma, chorionic carcinoma, clear cell carcinoma, colloid carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in situ, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma sim'plex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like.

In some instances, the methods of the present disclosure include treating a subject for cancer by administering the subject an effective amount of one or more delocalized lipophilic cation compounds.

Any useful delocalized lipophilic cation compounds may be employed in the subject methods. Non-limiting examples of useful delocalized lipophilic cation compounds include compounds (1), (2), (3), (4), (5), (6), (7), (8), (9), (10), and (11).

Subjects that may be administered a compound of the present disclosure may vary and may include subject's having a condition or suspected of having a condition. Conditions that a subject administered a compound of the present disclosure may have or may be suspected of having may vary and may include but are not limited to, e.g., neoplasia. In some instances, an individual to be treated according to the present methods will be an individual with a neoplasia. As used herein "neoplasia" includes any form of abnormal new tissue formation; and the like. In some cases, the individual has recently undergone treatment for neoplasia (e.g., cancer, a tumor, etc.) and are therefore at risk for recurrence. In some instances, the individual has not recently or previously undergone treatment for a neoplasia (e.g., cancer, a tumor, etc.) but has been newly diagnosed with a neoplasia. Any and all neoplasia are suitable neoplasia to be treated by the subject methods e.g., utilizing a delocalized lipophilic cation compound.

The compositions (e.g., those including one or more delocalized lipophilic cation compounds) of this disclosure can be supplied in the form of a pharmaceutical composition. Any suitable pharmaceutical composition may be employed, described in more detail below. As such, in some instances, methods of the present disclosure may include administering a delocalized lipophilic cation compound in a composition comprising an excipient (e.g., an isotonic excipient) prepared under sufficiently sterile conditions for administration to a mammal, e.g., a human.

Administration of a delocalized lipophilic cation compound to a subject, as described herein, may be performed employing various routes of administration. The route of administration may be selected according to a variety of factors including, but not necessarily limited to, the condition to be treated, the formulation and/or device used, the patient to be treated, and the like. Routes of administration that may be employed include but are not limited to oral and parenteral routes, such as oral, intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated.

Therapeutically effective doses of a subject compound or pharmaceutical composition can be determined by one of skill in the art, with a goal of achieving local (e.g., tissue) concentrations that are at least as high as the IC50 of an applicable compound disclosed herein.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Conversion of an animal dose to human equivalent doses (HED) may, in some instances, be performed using the conversion table and/or algorithm provided by the U.S. Department of Health and Human Services, Food and Drug Administration, Center for Drug Evaluation and Research (CDER) in, e.g., *Guidance for Industry: Estimating the Maximum Safe Starting Dose in Initial Clinical Trials for Therapeutics in Adult Healthy Volunteers* (2005) Food and Drug Administration, 5600 Fishers Lane, Rockville, MD 20857; (available at www(dot)fda(dot)gov/cder/guidance/index(dot)htm, the disclosure of which is incorporated herein by reference) (Table 1).

TABLE 1

Conversion of animal doses to human equivalent doses based on body surface area.

| Species | To Convert Animal Dose in mg/kg to Dose in mg/m², Multiply by $k_m$ | To Convert Animal Dose in mg/kg to HED[a] in mg/kg, Either: | |
|---|---|---|---|
| | | Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)0.33.
[b]This $k_m$ value is provided for reference only since healthy children will rarely be volunteers for phase 1 trials.
[c]For example, cynomolgus, rhesus, and stumptail.

The methods of treating a subject of the present disclosure include administering a delocalized lipophilic cation compound or a composition that included such a delocalized lipophilic cation compound to the subject in need thereof. In some cases, the pharmaceutical composition is administered by in intravenous injection, intramuscular injection or intraperitoneal injection.

In some cases, the subject in need of treatment with a delocalized lipophilic cation compound has a condition. In some cases, the condition is a bacteria infection. In some cases the condition is a neoplasia. In some cases, the neoplasia is a tumor. In some cases, the neoplasia is cancer. In some cases, the cancer is a breast cancer, an ovarian cancer, a colorectal cancer, a gastric cancer, a hepatic cancer, an esophageal cancer, a pancreatic cancer, a renal cell carcinoma, a prostate cancer, a brain tumor, a thyroid cancer, a bladder cancer, a head and neck cancer, a lung cancer or a blood cancer.

In some cases, the method of treating a subject includes administering a therapeutically effective amount of a delocalized lipophilic cation compound and treating the subject for the condition. In some cases, the administration of the therapeutically effective amount of the delocalized lipophilic cation compound inhibits a growth in a subject, such as e.g., growth of a bacterial infection in the subject or growth of a cancer in the subject.

In some embodiments, delocalized lipophilic cation compounds may find use in treating a subject by photodynamic therapy or photothermal therapy. The present disclosure provides a method of treating a subject that includes administering a therapeutically effective amount of a delocalized lipophilic cation compound to the subject and contacting the delocalized lipophilic cation compound in vivo with light. In some cases, contacting the delocalized lipophilic cation compound with the light causes the generation of reactive oxygen species. In some cases, the method kills at least one cancer cell. In some cases, the method reduces the size of a tumor. In some cases, the method reduces the growth of a tumor.

The delocalized lipophilic cation compounds of the present disclosure are fluorescent. Hence, delocalized lipophilic cation compounds of the present disclosure may find use in fluorescent endoscopy or fluorescent-guided surgery.

The present disclosure provides a method of treating a subject that includes administering a delocalized lipophilic cation compound to a subject and detecting a fluorescent signal produced by the administered delocalized lipophilic cation compound. In some cases, the compound is administered to the subject in an amount sufficient for fluorescence in vivo. In some cases, the fluorescent in vivo imaging includes fluorescent endoscopy, e.g. upper endoscopy. In some cases, the fluorescent endoscopy includes colonoscopy. In some cases, the method includes obtaining a biopsy from the subject and detecting a fluorescent signal from the administered compound in cells of the biopsy. In some cases, the biopsy is a cancer biopsy. In some cases, the cancer is resected and the method further comprises assessing surgical margins of the resected cancer by visualizing a fluorescent signal of the administered compound.

The present disclosure provides a method of killing a cell that includes contacting the cell with an effective amount of a delocalized lipophilic cation compound. In some case, the cell is a prokaryotic cell. In some cases, the cell is a eukaryotic cell, e.g. a plant cell, an animal cell. In some cases, the cell is a cancer cell. In some cases, the eukaryotic cell is a mammalian cell. In some cases, the mammalian cell is a cancer cell.

In some embodiments, methods of the present disclosure provide for fluorescently labeling the mitochondria of a cell. Such methods may include contacting a cell with an effective amount of a delocalized lipophilic cation compound. Various cells may be labeled according to such methods. In some cases, the cell is a cancer cell. In some case, the cell is a prokaryotic cell. In some cases, the cell is a eukaryotic cell, e.g. a plant cell, an animal cell, etc. In some cases, the eukaryotic cell is a mammalian cell. In some cases, the mammalian cell is a cancer cell.

The present disclosure provides methods of imaging cell mitochondria, comprising contacting a cell with an effective amount of a delocalized lipophilic cation compound and detecting a fluorescent signal from the compound. In some cases, the detecting is in vitro detecting. In some cases, the detecting comprises fluorescent imaging, including e.g., fluorescent microscopy. Various cells may be used with such methods. In some cases, the cell is a cancer cell. In some case, the cell is a prokaryotic cell. In some cases, the cell is a eukaryotic cell, e.g. a plant cell, an animal cell, etc. In some cases, the eukaryotic cell is a mammalian cell. In some cases, the mammalian cell is a cancer cell.

The present disclosure provides methods of determining whether or not a patient has a mitochondria related disease comprising contacting a cell of the patient with a delocalized lipophilic cation compound and detecting a fluorescent signal of the compound. In some cases, the contacting comprises administering the delocalized lipophilic cation compound to the patient. In some cases, the contacting comprises obtaining the cell from a biopsy and contacting the cell with the delocalized lipophilic cation in vitro. In some cases, the detecting comprises fluorescent in vivo imaging. In some cases, the fluorescent in vivo imaging comprises fluorescent endoscopy. In some cases, the fluorescent endoscopy comprises upper endoscopy. In some cases, the fluorescent endoscopy comprises colonoscopy.

In some methods of determining whether or not a patient has a mitochondria-related disease, the mitochondria related disease is mitochondrial myopathy; diabetes mellitus and deafness (DAD); Leber's hereditary optic neuropathy (LHON); Leigh syndrome; myoneurogenic gastrointestinal encephalopathy (MNGIE); myoclonic epilepsy with ragged red fibers (MERRF); neuropathy, ataxia, retinitis pigrnentosa, and ptosis (NARP); mitochondrial myopathy, encephalomyopathy, lactic acidosis, stroke-like symptoms (MELAS), mitochondrial neurogastrointestinal encephalopathy syndrome (MNGIE), or Friedrieich's ataxia.

The present disclosure provides methods of treating a patient for a mitochondria-related disease comprising determining whether or not a patient has a mitochondria-related disease, wherein the determining comprises contacting a cell of the patient with a delocalized lipophilic cation compound and detecting a fluorescent signal of the compound, and treating the patient for the disease if the patient was determined to have the mitochondria related disease. In some cases, the contacting comprises administering the delocalized lipophilic cation compound to the patient. In some cases, the contacting comprises obtaining the cell from a biopsy and contacting the cell with the delocalized lipophilic cation in vitro. In some cases, the detecting comprises fluorescent in vivo imaging. In some cases, the fluorescent in vivo imaging comprises fluorescent endoscopy. In some cases, the fluorescent endoscopy comprises upper endoscopy. In some cases, the fluorescent endoscopy comprises colonoscopy.

In some methods of treating a patient for a mitochondria related disease, the mitochondria related disease is mitochondrial myopathy; diabetes mellitus and deafness (DAD); Leber's hereditary optic neuropathy (LHON); Leigh syndrome; myoneurogenic gastrointestinal encephalopathy (MNGIE); myoclonic epilepsy with ragged red fibers (MERRF); neuropathy, ataxia, retinitis pigmentosa, and ptosis (NARP); mitochondrial myopathy, encephalomyopathy, lactic acidosis, stroke-like symptoms (MELAS), mitochondrial neurogastrointestinal encephalopathy syndrome (MNGIE), or Friedrieich's ataxia.

Kits

Also provided are kits for practicing one or more of the above-described methods and/or producing one or more of the above described compositions. The subject kits may vary greatly. Reagents and devices included in the subject kits may include those mentioned above with respect to the methods described, including e.g., methods of treating a subject, methods of labeling a cell, methods of killing a cell, etc. In the subject kits, the one or more components are present in the same or different containers, as may be convenient or desirable.

Kits of the present disclosure may include one or more reagents and/or devices for preparing a sample for processing and/or assaying, including e.g., for processing and/or assaying in a method as described herein. Useful reagents and/or devices that may be included in the subject kits include but are not limited to e.g., fixation reagents, fixation solution(s) that include at least one fixation reagent, a homogenization device, a device for generating a cell suspension, a device for incubating a cell suspension, a DNA labeling reagent, a device for obtaining a sample (e.g., a blood collection device, a biopsy device, an aspiration needle, etc.), and the like.

Kits of the present disclosure may include one or more reagents and/or devices for imaging a compound of the present disclosure. Such devices may vary and may include but are not limited to e.g., devices and/or reagents fluorescent endoscopy, devices and/or reagents fluorescent-guided surgery, and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

The subject delocalized lipophilic cation compounds find use a variety of applications, including but not limited to e.g., labeling cells, killing cells (including eukaryotic cells and prokaryotic cells), treating neoplasia, e.g. cancer, a tumor, etc. Without being bound by theory, an anti-cancer activity of delocalized lipophilic cation compounds may involve the selective accumulation of delocalized lipophilic cation compounds in the mitochondria of cancer cells relative to normal cells. In some cases, administration of a delocalized lipophilic cation compound to a subject with cancer can kill cancer cells, reduce proliferation and/or otherwise cause a reduction in size of the cancer. In some cases, administration of a delocalized lipophilic cation compound to a subject with cancer can cause a reduction in growth rate of the cancer.

In addition, many delocalized lipophilic cation compounds are fluorescent. Hence, such delocalized lipophilic cation compounds may find use in various applications that employ the detection of a fluorescent signal, such a but not limited to e.g., optical imaging, fluorescent image-guided surgery, fluorescence endoscopy, and the like. Methods and systems for fluorescent endoscopy are known in the art, e.g. those described in U.S. Pat. Nos. 4,821,117, 5,092,331, and 5,749,830, which are incorporated by reference. Methods and systems for fluorescent image-guided surgery are known in the art, e.g. those described in U.S. Patent Application Publications 2014/0276008, 2008/010339, and 2014/0276008, which are incorporated by reference.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as *Molecular Cloning: A Laboratory Manual,* 3rd Ed. (Sambrook et al., HaRBor Laboratory Press 2001); *Short Protocols in Molecular Biology,* 4th Ed. (Ausubel et al. eds., John Wiley & Sons 1999); *Protein Methods* (Bollag et al., John Wiley & Sons 1996); *Nonviral Vectors for Gene Therapy* (Wagner et al. eds., Academic Press 1999); *Viral Vectors* (Kaplift & Loewy eds., Academic Press 1995); *Immunology Methods Manual* (1. Lefkovits ed., Academic Press 1997); and *Cell and Tissue Culture: Laboratory Procedures in Biotechnology* (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

General Information

All air and moisture sensitive reactions were carried out in flame-dried glassware under a nitrogen atmosphere. Reactive liquid compounds were measured and transferred by gas-tight syringes and were added in the reaction flask through rubber septa. Tetrahydrofuran (THF) were freshly distilled from sodium benzophenoneketyl. Dichloromethane, toluene and DMF were distilled from CaH2. All standard synthesis reagents were purchased from Sigma-Aldrich Chemical Co. (St. Louis, MO) and used without further purification. The cell line was obtained from the American Type Tissue Culture Collection (Manassas, VA). Female athymic nude mice (nu/nu) were purchased from Charles River Laboratories (Boston, MA). Analytical thin layer chromatography was performed on glass-backed silica gel plates with F254 indicator. Compounds were visualized under UV lamp or by developing in iodine, vanillin, phosphomolybdic acid solution or with a potassium permanganate solution followed by heating on a hot plate to approximately 350° C. Flash chromatography was performed on 230-400 mesh silica gel with technical grade solvents which were distilled prior to use. $^1$H NMR spectra were recorded on a Bruker AV400 at 400 MHz as $CDCl_3$ solutions with tetramethylsilane ($\delta$=0 ppm) as the internal standard. $^{11}$C spectra were obtained on the same instruments at 100 MHz with $CDCl_a$($\delta$=77 ppm) as the internal reference. Chemical shifts are reported in parts per million (ppm). Multiplicities are reported as s (singlet), d (doublet), t (triplet), q (quartet), m (multiplet), dd (doublet of doublet), etc. High-resolution mass spectra were performed on Bruker APEX III 7.0 Tesla Ion Spec 4.7 Tesla FTMS and Thermo Scientific LTQ ORBITRAP XL. Matrix assisted laser desorption/ionization time of flight mass spectrometry (MALDI-TOF-MS) by Stanford Protein and Nucleic Acid Biotechnology Facility, Stanford University. Analytical or preparative high performance liquid chromatography (HPLC) was performed on a DIONEX ultimate 3000 instrument with PDA detection.

Example 1: Synthesis of Delocalized Lipophilic Cation Compounds

Compounds (1) through (11) were synthesized according to the synthetic scheme shown in FIG. 1. 1, 4-dimethylpyridium iodide (1.1 mmol) and the different indole-3-carboxaldehyde derivatives (1 mmol) were added into 10 mL of methanol. After stirring for ten minutes, catalytic amounts of piperidine (0.2 mmol) were added into the mixture. Under nitrogen protection, the reaction solutions were heated to reflux and kept at reflux for 4 to 24 hours, depending on the derivative. The reaction solution changed from light yellow to dark brown, with brown precipitates also forming. Thin layer chromatography analysis was used to detect the reaction endpoint. After the indole-3-carboxaldehyde derivatives disappeared, the reactions were stopped.

The products were purified either through using ether recrystallization and semi-preparative HPLC. For recrystallization, the corresponding precipitates were collected, washed with methanol and recrystallized in acetonitrile, giving an orange or brown powder as the product. For the semi-preparative HPLC purification, a Dionex Summit high-performance liquid chromatography (HPLC) system (Dionex Corporation, Sunnyvale, CA) with a 340U four-channel UV-Vis absorbance detector, reverse-phase semi-preparative HPLC column Zorbax SB (C18, 9.4 mm×250 mm) was used. The mobile phase was water and acetonitrile (both containing 0.1% TFA). The flow was 3 mL/min with gradient elution starting from 5% acetonitrile and ending up with 95% acetonitrile at 27 mins. 254 nm and 650 nm were used as the detection wavelength.

The purity of compounds (1) through (11) were detected by analysis HPLC with Dionex Acclaim 120 (C18, 4.6 mm×250 mm) analysis column, 1 mL/min flow rate, running the same gradient. All products are above 98% purity. All NMR spectra (1H, 13C) were performed on a Varian XL-400 (Varain, Palo Alto, CA). Electron spray ionization (ESI) mass spectrometry was performed.

Example 2: Absorbance and Fluorescence of Delocalized Lipophilic Cation Compounds The absorbance and fluorescence of delocalized lipophilic cation compounds (1) through (11) were measured. UV absorbance of the compounds was recorded on an Agilent 8453 UV spectrophotometer at a concentration of 31 μM in water. Fluorescence was recorded on a Fluoromax-3 spectrafluorometer (Jobin Yvon) at a concentration of 7.8 μM in water.

Figure 2A:
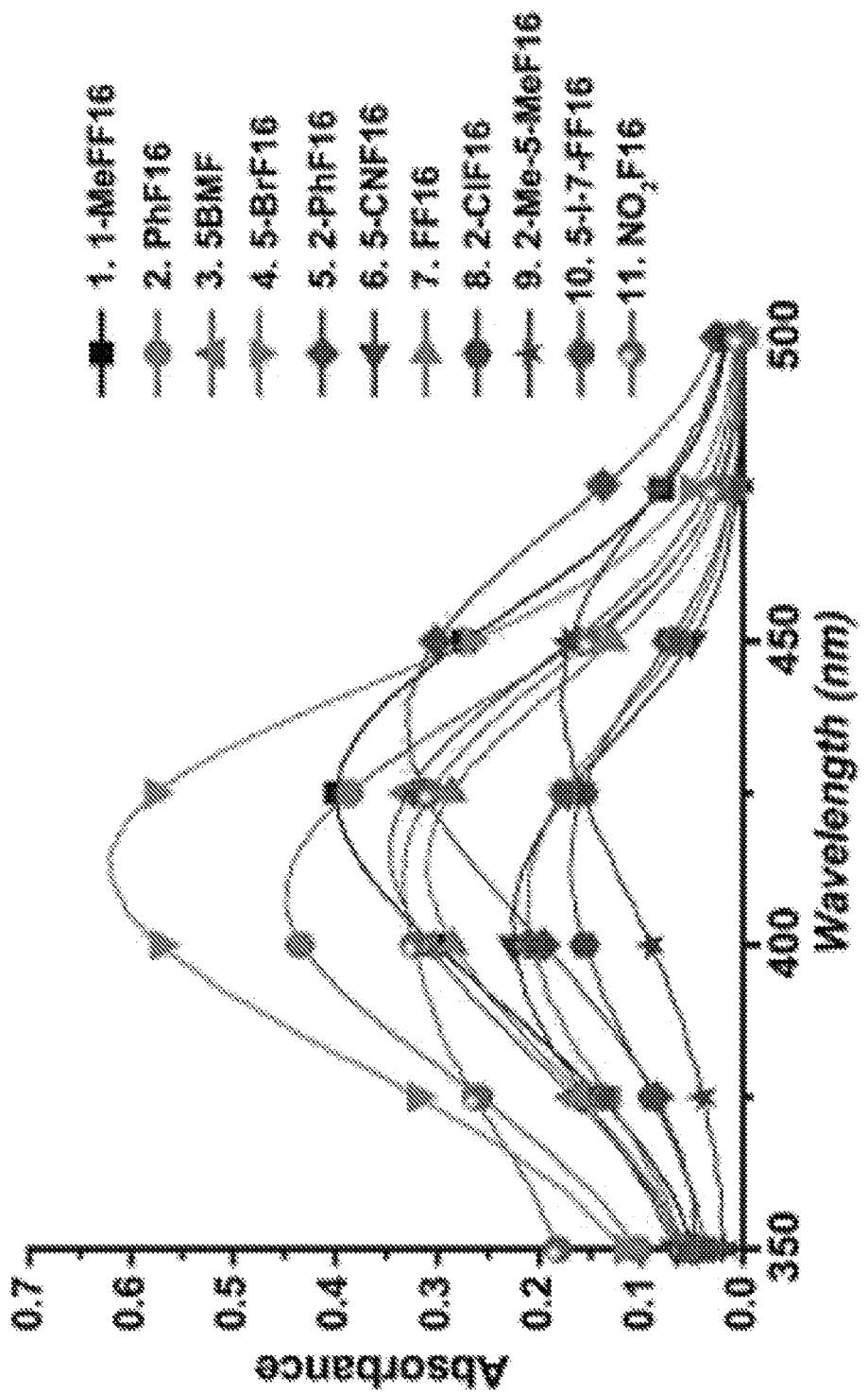
FIG. 2A shows the fluorescent absorption spectra of compounds (1) through (11).
Figure 2B:
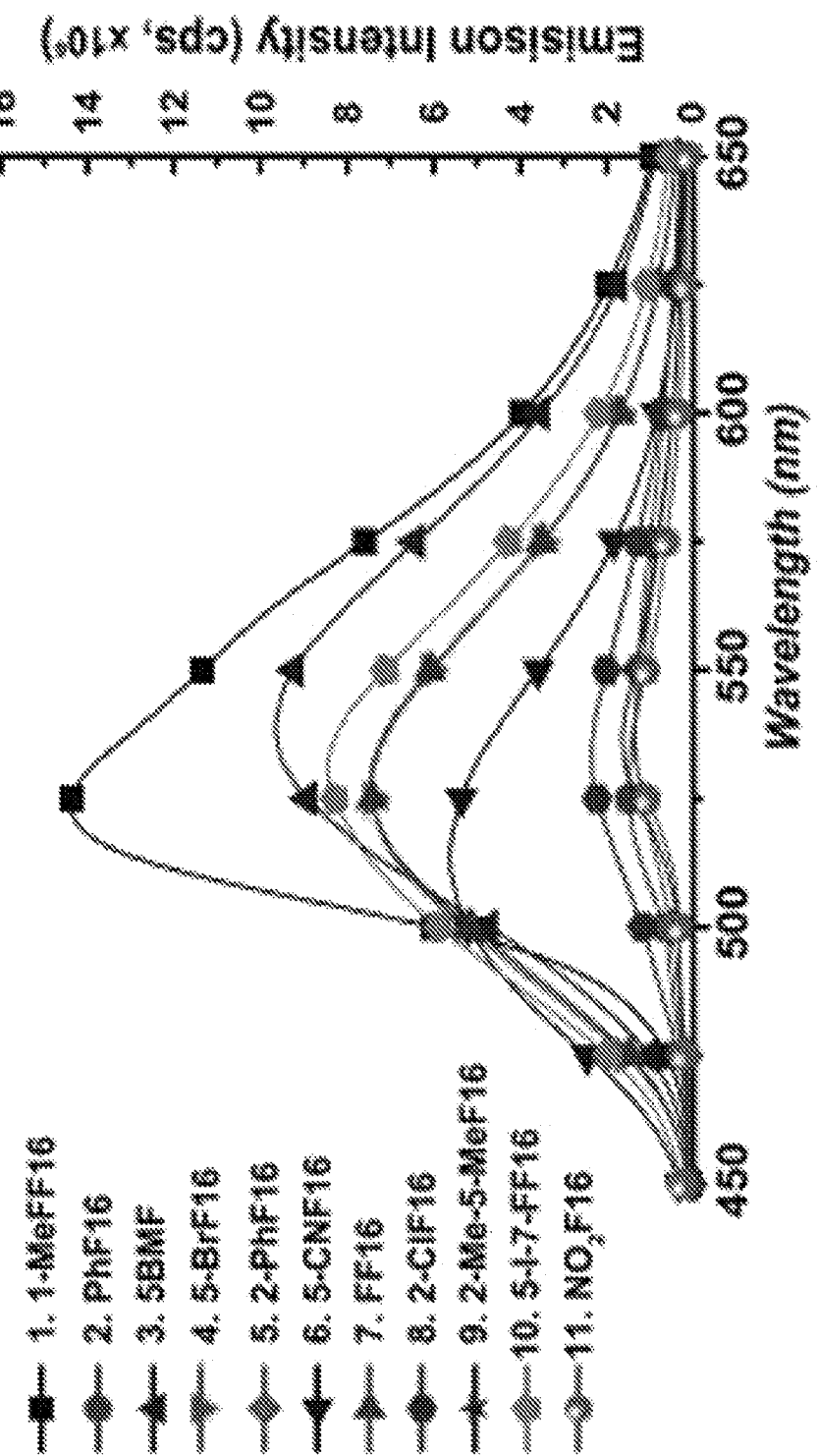
FIG. 2B shows the fluorescent emission spectra of compounds (1) through (11).

The absorbance of the compounds at wavelengths between 350 nm and 500 nm is shown in FIG. 2A. The absorption peaks of all compounds were approximately 425 nm, except compounds (5) and (9) which had absorption maxima of about 450 nm. The fluorescent emission spectra of the compounds are shown in FIG. 2B. The fluorescence maxima of the compounds was approximately 525 nm.

The quantum yield of compounds (1) through (11) was measured in ethanol using Rhodamine 6G as a reference. The observed quantum yields are shown in FIG. 2C. Compound (4) showed the highest quantum yield at 49.1%.

Example 3: Photostability of Delocalized Lipophilic Cation Compounds

The photostability of compounds (1) through (5), (7) through (9), (11), Mitotracker® Green, and Rhodamine 6G were assessed. Compounds (2), (3), (4), (5), (7), and (11) have similar photostability to Rhodamine 6G and Mitotracker® Green, while (1), (8), and (9) bleached relatively easily.

A 75 W Xenon arc lamp (Hamamatsu, San Jose, California, USA) with 420-470 nm bond pass filter (MF445-45, Thorlabs, Newton, New Jersey, USA) was used as the light source for the F16 derivatives, Rhodamine 6G, and Mitotracker® Green. Analogously, a 540-580 nm bond pass filter (MF559-34, Thorlabs, Newton, New Jersey, USA) was used to excite Mitotracker Red. All the dyes were dissolved in water at a 10 μM concentration in 700 μL micro quartz cuvettes (10 mm, Sigma-Aldrich, St. Louis, MO, USA). They were continuously excited for 50 mins. During this period, the fluorescence intensity was measured every 5 mins at 525 nm (F16s, Rhodamine 6G, Mitotracker Green) or 600 nm (Mitotracker Red). Relative fluorescence intensity change was monitored over time.

Example 4: Quantum Yield of Delocalized Lipophilic Cation Compounds

The quantum yields of compounds (1) through (11) and Rhodamine 60 were assessed. Compound (4) demonstrates the highest quantum yield (49.1%). The quantum yield of compounds (3), (7), (9) is around 20%, (1), (2) around 12%, and (5), (6), (8), (10), (11) under 10%.

The fluorescence quantum yields of the compounds were determined using the formula ($\phi=\phi s(Fx/Fs)$ (As/Ax)), where $\phi$ is quantum yield, F is the integrated area under the corrected emission spectrum, and A is the absorbance at the excitation wavelength; the subscripts x and s refer to F16s and the standard, respectively. Rhodamine 6G (OF 95%) in ethanol was used as the standard. All compounds and Rhodamine 6G were dissolved in ethanol in 5 different concentrations with the absorbance lower than 0.1 at 425 nm. The corresponding 5 different fluorescences of the compounds and Rhodamine 6G were excited at 425 nm and the emission spectra from 450 nm to 650 nm were obtained for the following integrated area measurement. All data was analyzed using Origin Pro 9.0 software (OriginLab, Northampton, Massachusetts, USA) to get the compounds' final quantum yield.

Example 5: Mitochondrial Targeting Properties of Delocalized Lipophilic Cation Compounds The mitochondrial targeting properties of compounds (1) through (11) were tested. 3 µM compounds were added to cells grown in a MatTek glass-bottom culture dishes (Ashland, Massachusetts) for 1 h and washed with PBS (phosphate-buffered saline) three times. After replacement of the medium, cells were imaged using a fluorescent microscope (Zeiss) with a 63× oil or 20× objective lens (excited in the GFP channel).

Mitotracker@ Red (Molecular Probes) and Hoechst (Thermo Scientific) were added to the medium to stain the mitochondria and nuclei, following the manufacturer's procedures. Cells were photographed using a 63× oil or 20× objective lens.

Figure 2D:
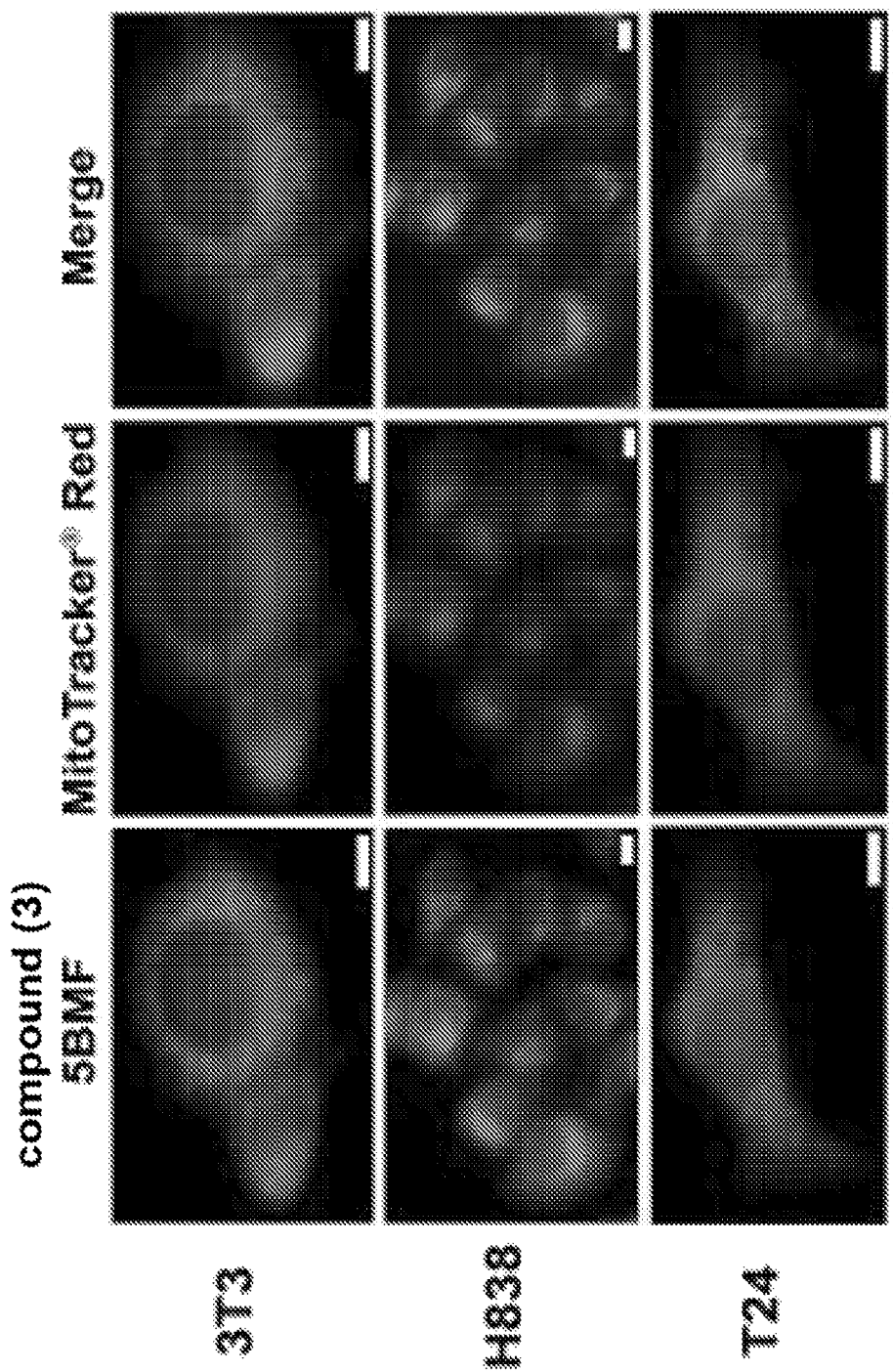
FIG. 2D shows the colocalization of compound (3) with a mitochondrial dye.

All compounds were found to stain the mitochondria in the tested cell lines. FIG. 2D shows the colocalization of compound (3) with MitoTrack in NIH-353, H838, and T24 cell lines.

Example 6: Examining Whether Accumulation of Delocalized Lipophilic Cation Compounds in Mitochondria is Caused by Mitochondrial Membrane Potential $\Delta\Psi m$)

Figure 3A:
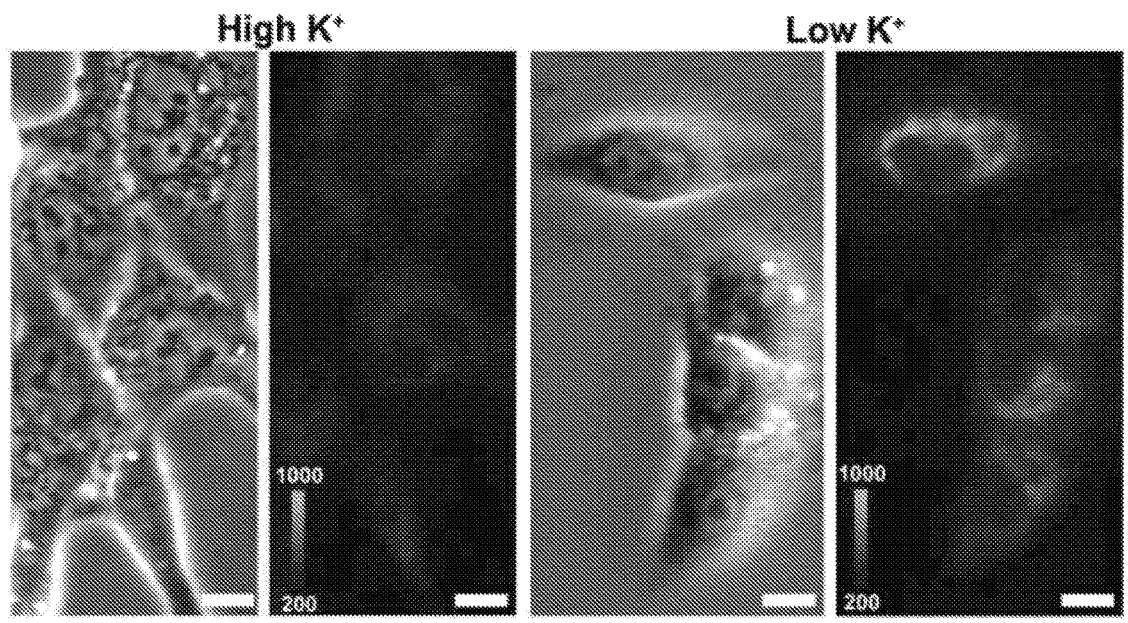
FIG. 3A shows the fluorescence of compound (3) in H838 cells that had been preincubated at low or high $K^+$ concentrations.

To examine whether the mitochondrial membrane potential ($\Delta\Psi m$) causes the accumulation of delocalized lipophilic cation compounds in mitochondria, H838 cells were preincubated with medium containing high concentrations of $K^+$ ions (i.e. 137 mM), to depolarize the mitochondrial membrane, or low concentrations of $K^+$ ions (i.e. 3 mM). Next, 3 µM of compound (3) was added and the cells were incubated for 30 minutes. Fluorescent analysis showed that low concentrations of $K^+$ ions resulted in more accumulation of compound (3) in the mitochondria, whereas less accumulation was observed with high $K^+$ concentrations (see FIGS. 3A, 3C).

Figure 3B:
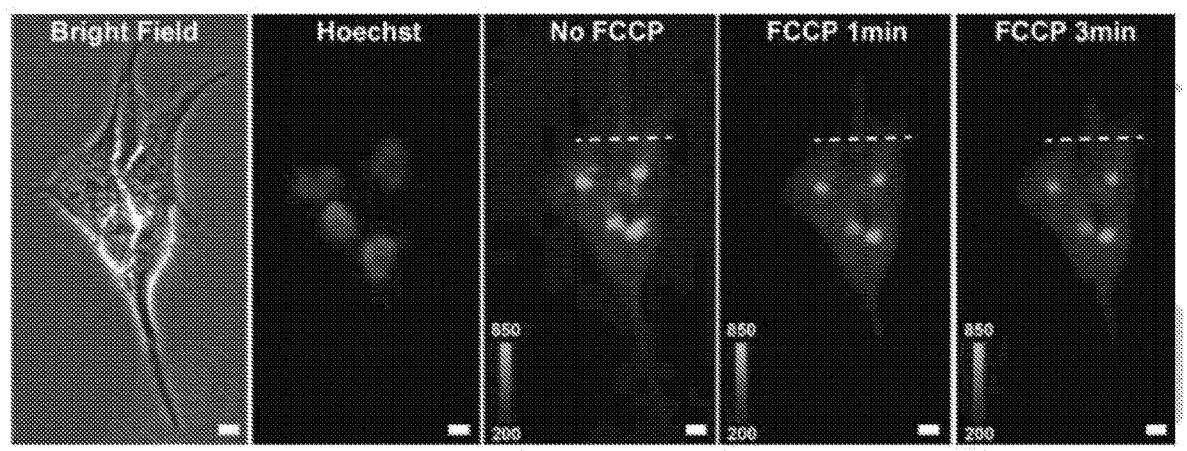
FIG. 3B shows the fluorescence of compound (3) in H838 cells that had been preincubated with $K^+$ after the addition of carbonyl cyanide p-(trifluoromethoxy) phenylhydrazone (FCCP).
Figure 3C:
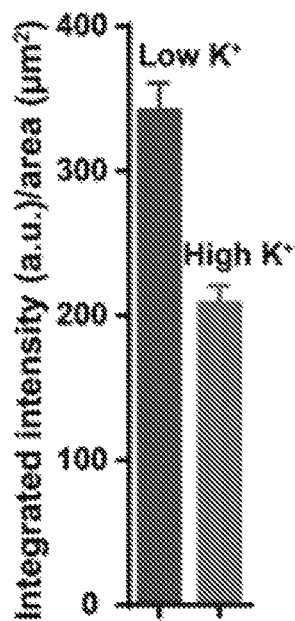
FIG. 3C shows the mean fluorescence density from compound (3) of cells that had been preincubated at low or high $K^+$ concentrations.
Figure 3D:
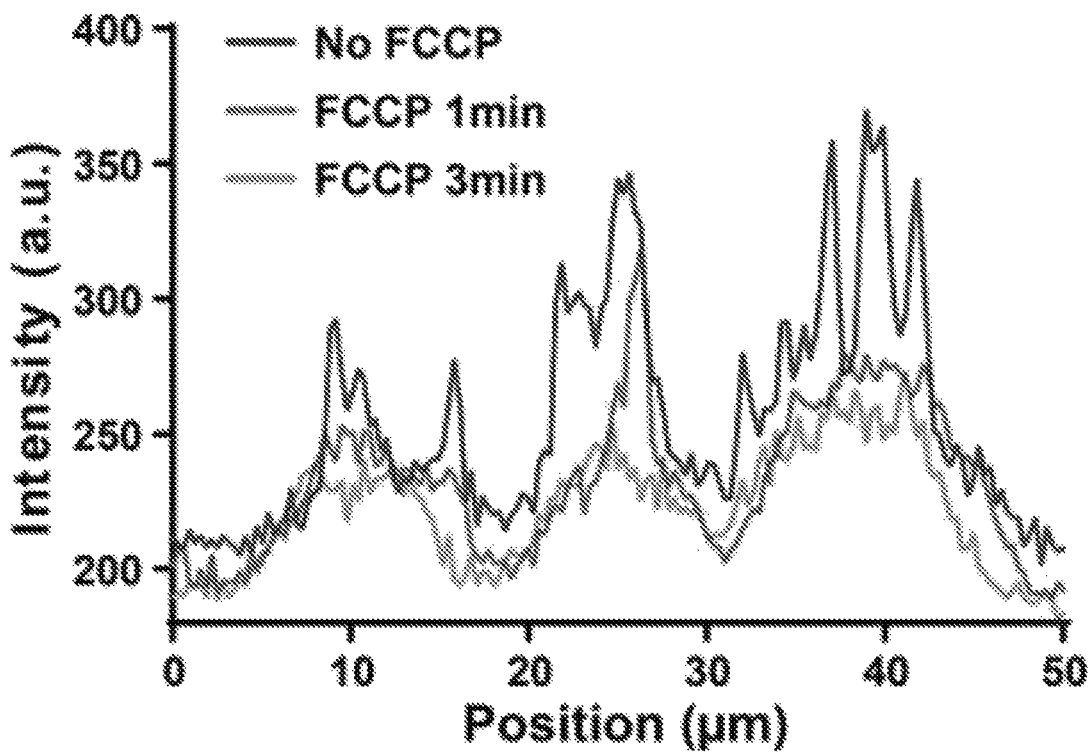
FIG. 3D shows the cross-sectional fluorescence intensity profiles taken along the white dashed-lines in FIG. 3B.

In addition, when carbonyl cyanide p-(trifluoromethoxy) phenylhdrazone (FCCP), a protonophore that dissipates the mitochondrial membrane potential, was added to the cells, the mitochondrial staining immediately decayed and diffused into the cytoplasm (FIGS. 3B and 3D). Hence, the selective accumulation of compound (3) to mitochondria is caused by the negative transmembrane potential of mitochondria.

Example 7: Cytotoxicity and Structure-Activity Relationship of Delocalized Lipophilic Cation Compounds The cytotoxicity of compounds (1) through (11) was tested in vitro with bladder cancer T24 cells, non-small cell lung cancer (NSCLC) H838 cells, and normal HIN-3T3 cells (FIG. 4). All test cell lines were incubated in 96-well plates overnight at a density of 3000 cells/well. The culture medium was replaced with 200 µL of culture medium, into which the testing compound was dispersed at various concentrations (1.95-500 µM). After incubating for 3 days, the viable cell numbers were checked and directly counted under microscopy (10×). A minimum of 1 mm×1 mm area was counted from each of at least three widely separated regions of cell culture. The cell proliferation rate was calculated by the following formula: cell proliferation rate (%)=(average cell number of sample wells/average cell number of control wells)×100%. The intact culture medium was evaluated as a control.

Six of the eleven compounds displayed strong anti-tumor activity, with $IC_{50}$ values within 0.36-6.2 µM (2, 3, 4, 5, 7, 10). Two of them showed selectivity indices larger than 10 (3, 7). Compound (3) had the best anti-tumor activity and relatively high selectivity, with $IC_{50}$ values for T24 and H838 cells of 0.82 µM and 0.36 µM, respectively.

Based on these cytotoxicity studies, a structure-activity relationship for delocalized lipophilic cation compounds was proposed. The following structure-activity relationship is described in terms of a delocalized lipophilic cation compound of formula (IV) wherein $R^{11}$ is methyl. $R^1$ substitution with methyl group decreases antitumor activity (ATAC) and normal cell toxicity (NCT), e.g. compare toxicity of (1) and (7). $R^2$ substitution increases NCT, e.g. compare (5) and (8). $R^4$ substitution by an electron-withdrawing group increases ATAC, and was the largest factor in ATAC, e.g. compare (4), (6), (7), and (11). $R^6$ substitution by an electron-donating group increases ATAC, e.g. compare (3), (4), and (10). Indole ring conjugation with an extended π system increases NCT and ATCA.

As such, it seems that modifying the distribution of electron density in the indole ring of delocalized lipophilic cation compounds plays a key role in determining the anti-tumor activity of such compounds.

Example 8: In Vivo Cytotoxicity and Effect on Body Mass of Compound (3)

In vivo studies on the effect of compound (3) on the tumor growth and body mass of a mouse model were conducted. Female athymic nude mice (nu/nu) from 4-6 weeks old were obtained from Charles River Laboratories (Boston, MA, USA) and kept under sterile conditions. $5\times10^6$ human lung adenocarcinoma HCC827 cells suspended in 150 µL of PBS were inoculated subcutaneously in the right shoulder of the nude mice. When the tumors reached 3~5 mm in diameter, the tumor bearing mice were administered i.v. with compound (3) (dissolved in 150 µL PBS, with 2 µL DMSO) at 15 mg/kg on days 1, 3, 5, 7, 9, 11, 13, 15, 17, 19, 21. Correspondingly, untreated tumor-bearing mice serving as controls were administered i.v. with 150 µL 1×PBS pH 7.4 (with 2 µL DMSO) on the same days as the treated mice. Ten mice were used for each group. Length and width of the elliptical tumors were measured by Vernier caliper after every intravenous injection. Modified ellipsoid formula ½ (Length×Width$^2$) was used to calculate the tumor size. The tumor growth was calculated with the ratio of final volume (FV) minus initial volume (IV) to initial volume (IV).

In vivo fluorescent imaging was taken 40 minutes and 2 hours after the injection of compound (3) 15 mg/kg. IVIS spectrum instrument was used. Excitation wavelength was set at 450 nm. Collection wavelength was set at 550 nm, using a 3s acquisition time. 4 mice for each group were used. Mice were sacrificed and the organs were harvest after each set of in vivo imaging. Fluorescent images of the organs were taken under the same settings.

FIG. 5A shows the results of the cytotoxicity studies of non-small cell lung cancer (NSCLC) cell line HCC827, along with the NSCLC cell lines H838, HCC4006, H1693, H2030, H2228, A549, H1437, and H1944. Compound (3)

showed impressively high ATCA in all these cell lines. Especially the H2228 cell line showed an $IC_{50}$ of 48.9 nM, in addition to the anti-cancer cell to anti-normal cell (3T3, FIG. 4a) ratio around 225 (FIG. 5A).

In addition, the HCC827 cell line was chosen for further in vivo study. FIG. 5B demonstrated typical fluorescent images of 2 h post intravenous injection (PI) of 15 mg/kg compound (3) into nude mice bearing subcutaneous HCC827 tumor. The tumor was clearly visualized from the surrounding background tissue with a tumor to background ratio of ~2, which was sufficient for fluorescent image-guided surgery. Tumor, kidney, bone, stomach, bowel, pancreas and skin accumulated more compound (3) compared with liver, spleen, heart, lung, and brain. The tumor to most normal organ ratios (2 h PI, ~2 to ~7) were high, especially high tumor/lung ratios observed, implying potential low lung tissue toxicity and use for tumor detection and fluorescent image-guided lung cancer surgery applications.

Furthermore, Figure 5C shows the treatment response of the HCC827 xenograft to intravenous (IV) injection with compound (3). As indicated by the mean tumor size in both control and treated groups, compound (3) exhibited significant ATCA at 21 days PI. The tumor volume of the compound (3) treated group (drug group) decreased dramatically compared to the PBS treated group (control group), with a statistically significant result (p=0.0426). Meanwhile the bodyweight between the control and treated group showed no significant difference (p=0.477) (FIG. 5D), implying low in vivo toxicity of compound (3). Flow cytometry results indicated that compound (3) inhibited carcinoma cell growth in a time-dependent manner. Tumor pathologic section H&E staining results displayed that compound (3) caused tumor inflammatory cell infiltration, fibrous tissue proliferation, and cell apoptosis.

Figure 6:
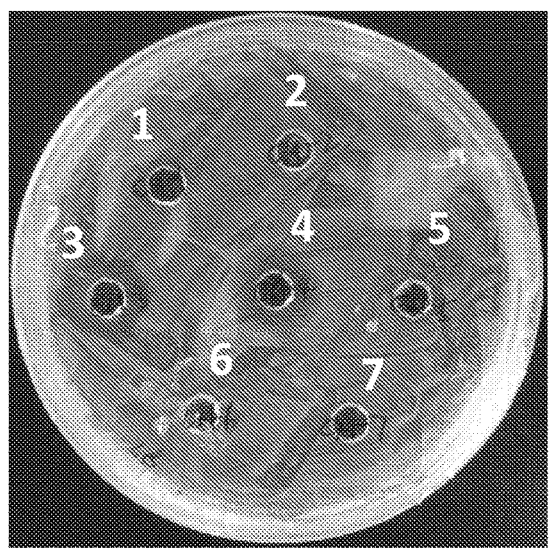
FIG. 6 shows the effects of compounds (1) through (11), in comparison to water and penicillin-streptomycin controls.
Figure 6:
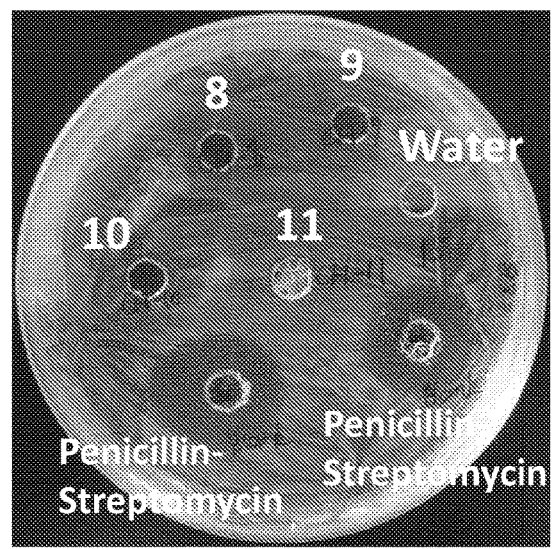

Example 9: Cytotoxicity and Cell Staining with Delocalized Lipophilic Cation Compounds The cytotoxicity of compounds (1) through (11) to *E. Coli* was assessed by contacting the *E. Coli* that had been cultured on a culture plate with the compounds. Controls were performed by contacting the *E. Coli* with samples of water and penicillin-streptomycin. Results of the cytotoxicity assay are shown in FIG. 6.

Figure 7:
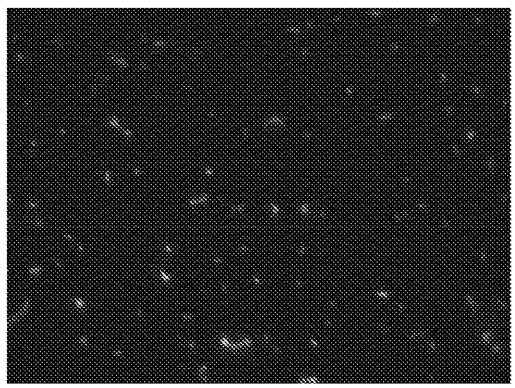
FIG. 7 shows the fluorescent labeling of *E. Coli* with compound (3).
Figure 7:
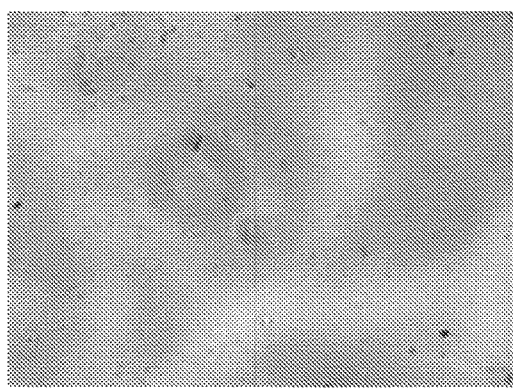
Figure 7:
Figure 7:
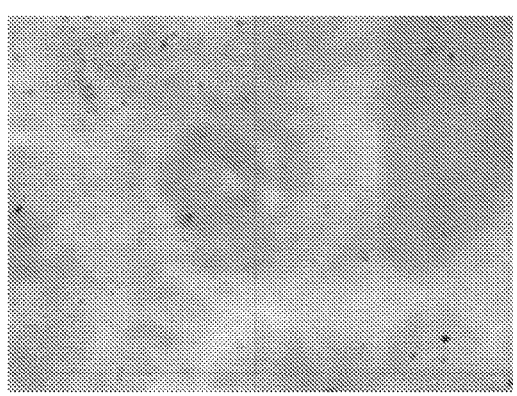

The ability of compound (3) to stain *E. Coli* was further assessed as shown in FIG. 7. Panels A and B show the staining as shown by GFP and Bright Field images. Panels C and D show the staining at pH 7.4, 1×PBS(Blank) with GFP and Bright Field images.

The ability of compound (6), i.e. "CN-F16", to stain *Arabidopsis thaliana* root was further assessed by contacting the root with compound (6), as shown in FIGS. 8 and 9. FIG. 8 images were captured 1 hour after contact whereas FIG. 9 images were captured 20 hours after contact. In both cases, a 10× microscope and a 20 ms exposure time were used. In both figures, Panels A-C show the root contacted with compound (6) whereas Panels D-F are controls. FIG. 10 shows the experimental setup used to capture *Arabidopsis thaliana* whole plant images.

Notwithstanding the appended claims, the disclosure is also defined by the following clauses:

Clause 1. A compound of the formula (I):

A-L-Z$^+$(I)

wherein:
A is selected from aryl, substituted aryl, heteroaryl and substituted heteroaryl;

L is a linker;
Z$^+$ is a group comprising a positive charge,
wherein the compound is a π-conjugated system.

Clause 2. The compound of claim 1, wherein A is selected from indole and substituted indole.

Clause 3. The compound of claim 1 or 2, wherein Z$^+$ is selected from a heteroaryl or substituted heteroaryl comprising a positive charge.

Clause 4. The compound of claim 3, wherein Z$^+$ is selected from pyridinium or substituted pyridinium.

Clause 5. The compound of any one of claims 1 to 4, wherein L is selected from alkenylene, alkynylene, arylene, alkarylene and aralkylene.

Clause 6. The compound of any one of claims 1 to 5, of the formula (11):

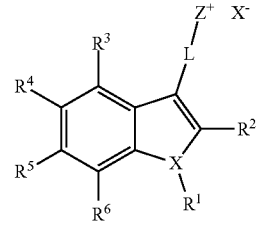

(II)

wherein,
X$^-$ is a counterion;
Z+ is a group comprising a positive charge;
L is a linker;
X is selected from CR$^8$ and N;
R$^1$ and R$^8$ are each independently selected from H, alkyl, substituted alkyl, alkenyl, substituted alkenyl, aryl, substituted aryl, heteroaryl and substituted heteroaryl;
R$^2$, R$^3$ and R$^d$ are each independently selected from H, alkyl, substituted alkyl, alkenyl, substituted alkenyl, aryl, substituted aryl, heteroaryl, substituted heteroaryl, halogen, nitro and nitrile;
R$^5$ and R$^6$ are each independently selected from H, alkyl, substituted alkyl, alkenyl, substituted alkenyl, aryl, substituted aryl, heteroaryl, substituted heteroaryl, halogen, nitro and nitrile; or R$^5$ and R$^6$ together with the carbon atoms to which they are attached form a fused ring selected from aryl, substituted aryl, heteroaryl and substituted heteroaryl.

Clause 7. The compound of any one of claims 1 to 6 of the formula (III):

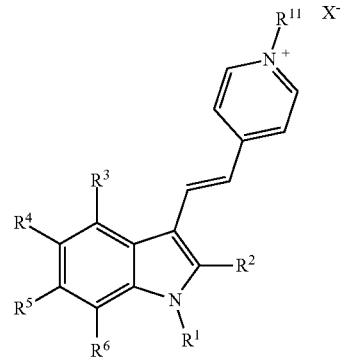

(III)

wherein,

X⁻ is a counterion;

X is selected from $CR^8$ and N;

$R^1$ and $R^3$ are each independently selected from H, alkyl, substituted alkyl, alkenyl, substituted alkenyl, aryl, substituted aryl, heteroaryl and substituted heteroaryl;

$R^2$, $R^3$ and $R^4$ are each independently selected from H, alkyl, substituted alkyl, alkenyl, substituted alkenyl, aryl, substituted aryl, heteroaryl, substituted heteroaryl, halogen, nitro and nitrile;

$R^5$ and $R^8$ are each independently selected from H, alkyl, substituted alkyl, alkenyl, substituted alkenyl, aryl, substituted aryl, heteroaryl, substituted heteroaryl, halogen, nitro and nitrile; or $R^5$ and $R^6$ together with the carbon atoms to which they are attached form a fused ring selected from aryl, substituted aryl, heteroaryl and substituted heteroaryl; and $R^{11}$ is selected from H, alkyl, substituted alkyl, alkenyl, substituted alkenyl, aryl, substituted aryl, heteroaryl and substituted heteroaryl.

Clause 8. The compound of claim 6 or 7, wherein one or more of $R^1$, $R^2$, $R^4$, $R^5$ and $R^6$ is a substituent other than hydrogen.

Clause 9. The compound of any one of claims 1 to 7 of the formula (IV):

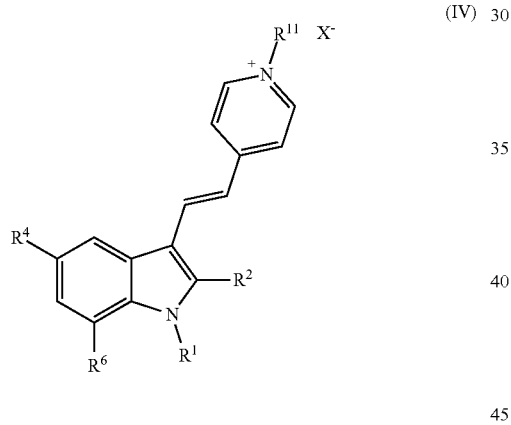

(IV)

wherein,

X⁻ is a counterion;

$R^1$ is selected from H, alkyl, substituted alkyl, alkenyl, substituted alkenyl, aryl, substituted aryl, heteroaryl and substituted heteroaryl;

$R^2$, $R^4$ and $R^6$ are each independently selected from H, alkyl, substituted alkyl, alkenyl, substituted alkenyl, aryl, substituted aryl, heteroaryl, substituted heteroaryl, halogen, nitro and nitrile; and $R^{11}$ is selected from H, alkyl, substituted alkyl, alkenyl, substituted alkenyl, aryl, substituted aryl, heteroaryl and substituted heteroaryl.

Clause 10. The compound of any one of claims 1 to 9 wherein $R^1$ is H.

Clause 11. The compound of any one of claims 1 to 10, wherein $R^4$ is bromide.

Clause 12. The compound of any one of claims 1 to 11, wherein $R^6$ is methyl.

Clause 13. The compound of any one of claims 6 to 12, wherein the counterion is iodide.

Clause 14. The compound of any one of claims 1 to 13, selected from the structures:

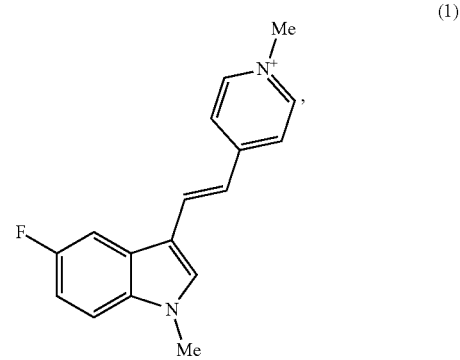

(1)

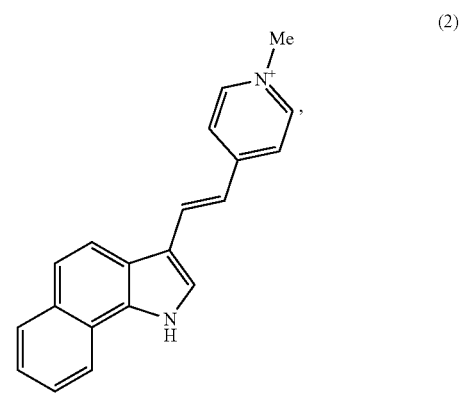

(2)

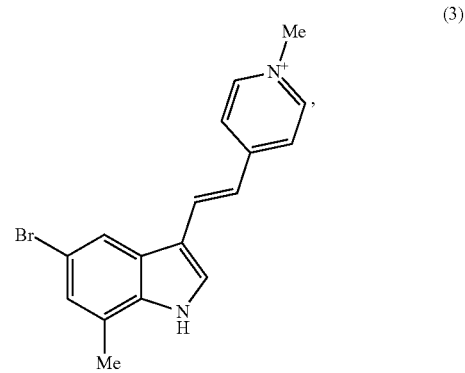 [SMILES: Cc1cc(Br)cc2c(/C=C/c3cc[n+](C)cc3)c[nH]c12]

(3)

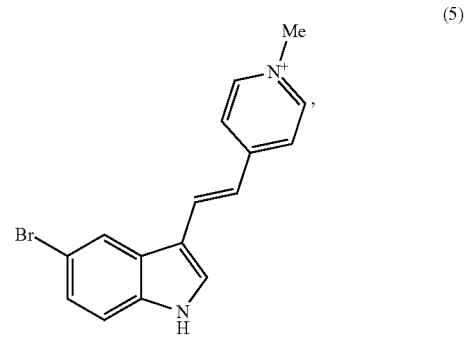

(5)

(6) 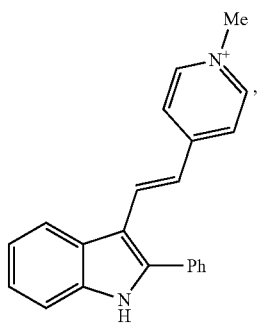

(4) 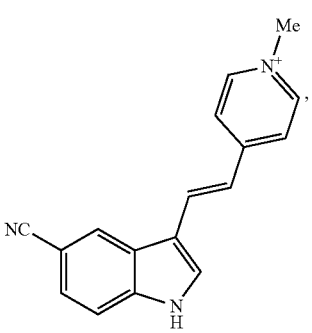

(7) 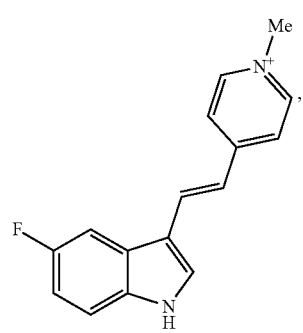

(8) 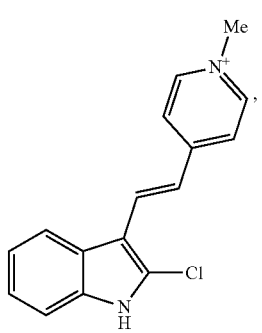

(9) 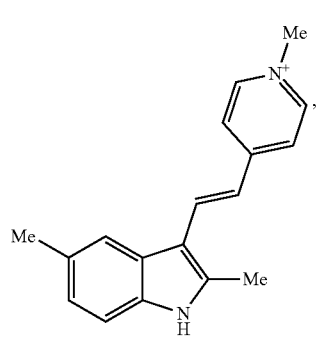

(10) 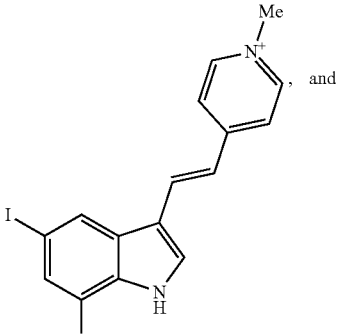, and

(11) 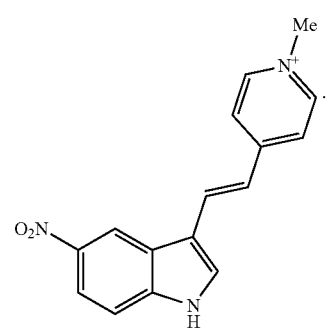

Clause 15. The compound of claim 14, of the structure:

(3) 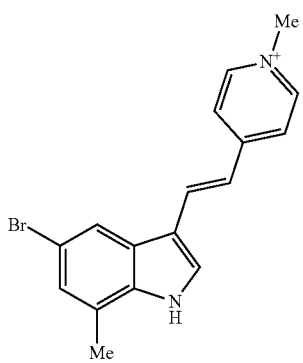 [SMILES: Cc1cc(Br)cc2c(/C=C/c3cc[n+](C)cc3)c[nH]c12]

Clause 16. The compound of any one of claims 1 to 15, wherein the compound is selectively cytotoxic to cancer cells.

Clause 17. The compound of any one of claims 1 to 16, wherein the compound has an $IC_{50}$ for cancer cells of less than 10 μM.

Clause 18. The compound of claim 17, wherein the $IC_{50}$ for cancer cells is 500 nM or less.

Clause 19. The compound of any one of claims 1 to 18, wherein the compound has an $IC_{50}$ for non-cancerous cells that is at least double the $IC_{50}$ for cancer cells.

Clause 20. The compound of any one of claims 1 to 19, wherein the compound has a fluorescence absorbance peak between 375 nm and 475 nm and a fluorescence emissions peak between 475 nm and 575 nm.

Clause 21. The compound of any one of claims 1 to 20, wherein the compound has as fluorescence quantum yield of 10% or more relative to a Rhodamine 6G reference.

Clause 22. The compound of any one of claims 1 to 21, wherein the compound is a derivative of F16.

Clause 23. A pharmaceutical composition, comprising:
a compound of any one of claims 1-22; and
a pharmaceutically acceptable excipient.

Clause 24. A method comprising administering the pharmaceutical composition of claim 23 to a subject in need thereof.

Clause 25. The method of claim 24, wherein the pharmaceutical composition is administered by intravenous injection, intramuscular injection or intraperitoneal injection.

Clause 26. The method of claims 24 or 25, wherein the subject has a condition.

Clause 27. The method of claim 26, wherein the condition is a bacterial infection.

Clause 28. The method of claim 26, wherein the condition is a cancer.

Clause 29. The method of claim 28, wherein the cancer is a breast cancer, an ovarian cancer, a colorectal cancer, a gastric cancer, a hepatic cancer, an esophageal cancer, a pancreatic cancer, a renal cell carcinoma, a prostate cancer, a brain tumor, a thyroid cancer, a bladder cancer, a head and neck cancer, a lung cancer or a blood cancer.

Clause 30. The method of any one of claims 26 to 29, wherein the method comprises administering a therapeutically effective amount of the composition and treating the subject for the condition.

Clause 31. The method of claim 30, wherein the therapeutically effective amount inhibits growth of a bacterial infection in the subject or growth of a cancer in the subject.

Clause 32. The method of any one of claims 24 to 31, wherein the method comprises detecting a fluorescent signal of the administered compound.

Clause 33. The method of claim 32, wherein the composition is administered to the subject in an amount sufficient for fluorescent in vivo imaging.

Clause 34. The method of claim 33, wherein the fluorescent in vivo imaging comprises fluorescent endoscopy.

Clause 35. The method of claim 34, wherein the fluorescent endoscopy comprises upper endoscopy.

Clause 36. The method of claim 34, wherein the fluorescent endoscopy comprises colonoscopy.

Clause 37. The method of any of claims 24 to 36, wherein the method further comprises obtaining a biopsy from the subject and detecting a fluorescent signal of the administered compound in cells of the biopsy.

Clause 38. The method of claim 37, wherein the biopsy is a cancer biopsy.

Clause 39. The method of any of claims 28 to 38, wherein the cancer is resected and the method further comprises assessing surgical margins of the resected cancer by visualizing a fluorescent signal of the administered compound.

Clause 40. A method of killing a cell, the method comprising contacting the cell with an effective amount of a compound of any one of claims 1-22.

Clause 41. The method of claim 40, wherein the cell is a prokaryotic cell.

Clause 42. The method of claim 40, wherein the cell is a eukaryotic cell.

Clause 43. The method of claim 42, wherein the eukaryotic cell is a plant cell.

Clause 44. The method of claim 42, wherein the eukaryotic cell is a mammalian cell.

Clause 45. The method of claim 44, wherein the mammalian cell is a cancer cell.

Clause 46. A method of fluorescently labeling the mitochondria of a cell, the method comprising contacting the cell with an amount of an effective amount of a compound of any one of claims 1-22.

Clause 47. The method of claim 46, wherein the cell is a prokaryotic cell.

Clause 48. The method of claim 46, wherein the cell is a eukaryotic cell.

Clause 49. The method of claim 48, wherein the eukaryotic cell is a plant cell.

Clause 50. The method of claim 48, wherein the eukaryotic cell is a mammalian cell.

Clause 51. The method of claim 50, wherein the mammalian cell is a cancer cell.

Clause 52. The method of any one of claims 46 to 51, wherein the method further comprises exposing the contacted cell with a light of an excitation wavelength to detect a fluorescent signal of an emission wavelength from the compound, thereby visualizing the fluorescently labeled the mitochondria of the cell.

Clause 53. A kit comprising the compound of any one of claims 1-22.

Clause 54. The kit of claim 53, wherein the kit further comprises pharmaceutically acceptable excipient.

Clause 55. The kit of claims 53 or 54, further comprising a delivery device.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A compound of formula (III):

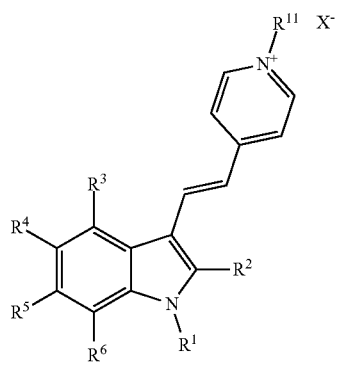

wherein,

X⁻ is a counterion;

$R^1$ and $R^8$ are each independently selected from H, alkyl, substituted alkyl, alkenyl, substituted alkenyl, aryl, substituted aryl, heteroaryl and substituted heteroaryl;

$R^2$ and $R^3$ are each independently selected from H, alkyl, substituted alkyl, alkenyl, substituted alkenyl, aryl, substituted aryl, heteroaryl, substituted heteroaryl, halogen, nitro and nitrile;

$R^5$ and $R^6$ are each independently selected from H, alkyl, substituted alkyl, alkenyl, substituted alkenyl, aryl, substituted aryl, heteroaryl, substituted heteroaryl, halogen, nitro and nitrile; or $R^5$ and $R^6$ together with the carbon atoms to which they are attached form a fused ring selected from aryl, substituted aryl, heteroaryl and substituted heteroaryl;

$R^4$ is selected from substituted alkyl, alkenyl, substituted alkenyl, aryl, substituted aryl, heteroaryl, substituted heteroaryl, nitro and nitrile if $R^6$ is H; or $R^4$ is selected from H alkyl, substituted alkyl, alkenyl, substituted alkenyl, aryl, substituted aryl, heteroaryl, substituted heteroaryl, halogen, nitro and nitrile if R6 is not H and if $R^4$ is H or F then $R^6$ is not methyl; and $R^{11}$ is selected from H, alkyl, substituted alkyl, alkenyl, substituted alkenyl, aryl, substituted aryl, heteroaryl and substituted heteroaryl.

2. The compound of claim 1, of the formula (IV):

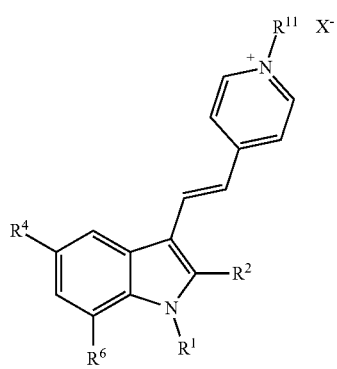

wherein,

X⁻ is a counterion;

$R^1$ is selected from H, alkyl, substituted alkyl, alkenyl, substituted alkenyl, aryl, substituted aryl, heteroaryl and substituted heteroaryl;

$R^2$ and $R^6$ are each independently selected from H, alkyl, substituted alkyl, alkenyl, substituted alkenyl, aryl, substituted aryl, heteroaryl, substituted heteroaryl, halogen, nitro and nitrile;

$R^4$ is selected from substituted alkyl, alkenyl, substituted alkenyl, aryl, substituted aryl, heteroaryl, substituted heteroaryl, nitro and nitrile if $R^6$ is H; or $R^4$ is selected from H, alkyl, substituted alkyl, alkenyl, substituted alkenyl, aryl, substituted aryl, heteroaryl, substituted heteroaryl, halogen, nitro and nitrile if $R^6$ is not H;

and $R^{11}$ is selected from H, alkyl, substituted alkyl, alkenyl, substituted alkenyl, aryl, substituted aryl, heteroaryl and substituted heteroaryl.

3. The compound of claim 1, selected from the structures:

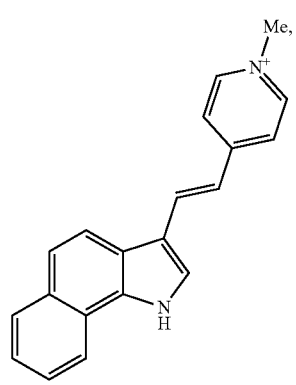

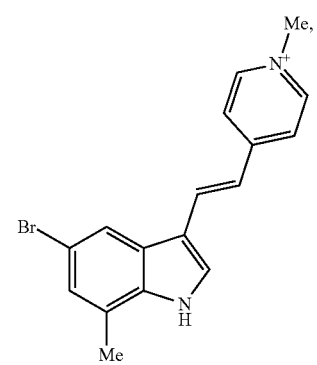

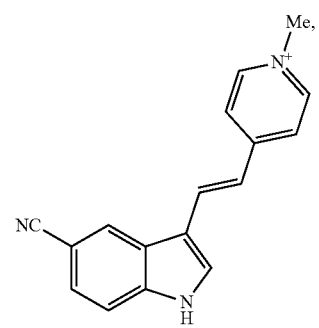

-continued

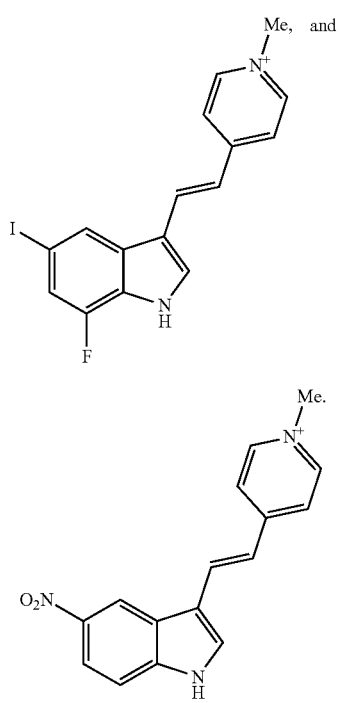

(10)

(11)

4. The compound of claim 1, wherein the compound is selectively cytotoxic to cancer cells.

5. A pharmaceutical composition, comprising:
 a) a compound of claim 1; and
 b) a pharmaceutically acceptable excipient.

6. A method of killing a cell, the method comprising contacting the cell with an effective amount of a compound of claim 1.

7. A method of fluorescently labeling the mitochondria of a cell, the method comprising contacting the cell with an effective amount of a compound of claim 1.

8. A kit comprising the compound of claim 1.

9. The compound of claim 3, wherein the compound is:

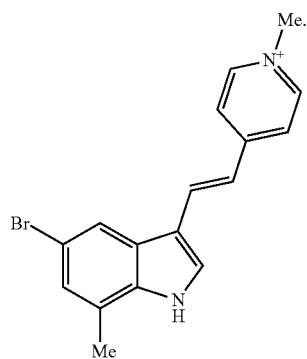

10. The compound of claim 4, wherein the compound has an IC50 value of 10 μM or less.

* * * * *